(12) United States Patent
Narimatsu et al.

(10) Patent No.: US 7,470,529 B2
(45) Date of Patent: Dec. 30, 2008

(54) CHONDROITIN SYNTHASE AND NUCLEIC ACID ENCODING THE ENZYME

(75) Inventors: Hisashi Narimatsu, Tsukuba (JP); Koji Kimata, Nagoya (JP); Toshikazu Yada, Kuwana (JP); Takashi Sato, Tsukuba (JP); Masanori Goto, Tsukuba (JP)

(73) Assignees: Seikagaku Kogyo Kabushiki Kaisha, Tokyo (JP); National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 11/748,409

(22) Filed: May 14, 2007

(65) Prior Publication Data

US 2008/0070996 A1    Mar. 20, 2008

Related U.S. Application Data

(62) Division of application No. 10/516,100, filed as application No. PCT/JP03/06880 on May 30, 2003, now Pat. No. 7,232,676.

(30) Foreign Application Priority Data

May 31, 2002  (JP)  ............... 2002-160855
May 6, 2003   (JP)  ............... 2003-128344

(51) Int. Cl.
C12P 9/10     (2006.01)
C12P 21/06    (2006.01)
C12N 15/63    (2006.01)
C12N 1/10     (2006.01)
C07H 21/00    (2006.01)

(52) U.S. Cl. ............. 435/193; 435/69.1; 435/84; 435/254.11; 435/320.1; 435/325; 435/252.3; 536/23.2

(58) Field of Classification Search ............... None
See application file for complete search history.

(56) References Cited

U.S. PATENT DOCUMENTS

2003/0104601 A1  6/2003  DeAngelis

FOREIGN PATENT DOCUMENTS

JP          2003-199583 A     7/2003

OTHER PUBLICATIONS

XP-002333486, "*Homo sapiens* chromosome 5 clone CTB-140F24, Working Draft Sequence, 5 unordered pieces" (abstract), Mar. 16, 2000.
XP-002333487, "Human chondroitin synthetase protein SEQ ID No. 2" (abstract), Feb. 26, 2004.
Supplementary Partial European Search Report dated Jul. 12, 2005.
Kitagawa H. et al, "Characterization of serum bata-glucuronyl transferase involved in chondroitin sulfate biosynthesis" Glycobiology 1997 vol. 7 No. 7, pp. 905-911.
Rohmann K. et al, "Two N-acetylgalactosaminyltransferase are involved in the biosynthesis of chondroitin sulfate" Eur. J. Biochem, 1985, vol. 148 No. 3, pp. 463-469.
Hiroshi et al., "Molecular Cloning and Expression of a Human Chondroitin Synthase", (JBC, 2001, 276, pp. 38721-38726).
Kamakari et al. (Gene bank—Accession No. AJ504664, Feb. 17, 2003).

*Primary Examiner*—Rebecca E. Prouty
*Assistant Examiner*—MD. Younus Meah
(74) *Attorney, Agent, or Firm*—Sughrue Mion, PLLC

(57) ABSTRACT

A human-derived novel chondroitin synthase, which is an enzyme for synthesizing a fundamental backbone of chondroitin and has both glucuronic acid transferring activity and N-acetylgalactosamine transferring activity.

7 Claims, 9 Drawing Sheets

US 7,470,529 B2

CHONDROITIN SYNTHASE AND NUCLEIC ACID ENCODING THE ENZYME

This is a divisional of application Ser. No. 10/516,100 filed Nov. 30, 2004 now U.S. Pat. No. 7,232,676, which is a National Stage application of PCT Application No. PCT/JP03/06880, filed May 30, 2003, which claims priority of Japanese Application Nos. JP 2002-160855, filed May 31, 2002, and JP 2003-128344, filed May 6, 2003, the disclosure of each of which is incorporated herein by reference in its entirety.

TECHNICAL FIELD

The present invention relates to an enzyme which synthesizes a sugar chain backbone of chondroitin/chondroitin sulfate (fundamental backbone: hereinafter also referred to as "chondroitin backbone") and a DNA encoding the enzyme. More particularly, the present invention relates to an enzyme which transfers a D-glucuronic acid residue to an N-acetyl-D-galactosamine residue when the N-acetyl-D-galactosamine residue is present at the non-reducing end of the chondroitin backbone, or transfers an N-acetyl-D-galactosamine residue to a D-glucuronic acid residue when the D-glucuronic acid residue is present at the non-reducing end, and a DNA encoding the enzyme.

BACKGROUND OF THE INVENTION

In the present specification, regarding sugars and sugar residues as used herein, all optical isomers are D-isomers, unless otherwise indicated.

Chondroitin sulfate and chondroitin are kinds of glycosaminoglycans having, as the fundamental backbone, a repeating structure of a disaccharide of a D-glucuronic acid residue (hereinafter sometimes simply referred to as "glucuronic acid" or "GlcUA") and an N-acetyl-D-galactosamine residue (hereinafter sometimes simply referred to as "N-acetyl-galactosamine" or "GalNAc") (i.e., -[GlcUAβ(1,3)-GalNAcβ(1,4)-]$_n$; n is an integer of 2 or more).

Until now, glycosaminoglycans, particularly chondroitin and chondroitin sulfate, have been extracted and purified from cartilages, organs and the like in animals. However, due to shortage of the materials, a method for artificially synthesizing a chondroitin backbone common to chondroitin and chondroitin sulfate has been recently studied. Particularly, a method using a human-derived enzyme is preferred since a bio-defense mechanism such as an antigen-antibody reaction does not strongly occur even when the artificially synthesized chondroitin or chondroitin sulfate is contaminated with the enzyme. At present, only one enzyme is known as the enzyme for synthesizing such a chondroitin backbone, particularly an enzyme which is derived from human and has both GlcUA transferring activity and GalNAc transferring activity (*J. Biol. Chem.*, 276, 38721-38726 (2001)).

It is considered that use of a cocktail system containing several types of enzymes is preferred for the synthesis of the chondroitin backbone. This is because the different optimum reaction conditions of respective enzymes can relax the reaction conditions of the general reaction system. However, only the above-described enzyme is known at present as an enzyme which is derived from human and has both GlcUA transferring activity and GalNAc transferring activity, and it is the present situation that studies on the synthesis of the chondroitin backbone are insufficient because of the difficulty in strictly controlling the conditions.

Accordingly, a human-derived novel enzyme which is an enzyme for synthesizing a chondroitin backbone and has both GlcUA transferring activity and GalNAc transferring activity has been desired.

DISCLOSURE OF THE INVENTION

The present invention relates to the following (1) to (14).

(1) A chondroitin synthase which consists of a polypeptide consisting of the amino acid sequence represented by SEQ ID NO:2 or an amino acid sequence consisting of amino acid numbers 130 to 882 in the amino acid sequence represented by SEQ ID NO:2, or a sugar chain-bound polypeptide in which a sugar chain is bound to the polypeptide.

(2) A chondroitin synthase comprising a polypeptide which has enzyme activity of transferring an N-acetyl-D-galactosamine residue to an N-acetyl-D-galactosamine acceptor or enzyme activity of transferring a D-glucuronic acid residue to a D-glucuronic acid acceptor, and consists of an amino acid sequence having substitution, deletion, insertion, addition and/or transposition of 1 to 150 amino acid residues in an amino acid sequence consisting of amino acid numbers 130 to 882 in the amino acid sequence represented by SEQ ID NO:2.

(3) The chondroitin synthase according to (2), which has enzyme activity of transferring an N-acetyl-D-galactosamine residue from an N-acetyl-D-galactosamine donor to a D-glucuronic acid residue of chondroitin having the D-glucuronic acid residue at the non-reducing end, and has enzyme activity of transferring a D-glucuronic acid residue from a D-glucuronic acid donor to an N-acetyl-D-galactosamine residue of chondroitin having the N-acetyl-D-galactosamine residue at the non-reducing end.

(4) A nucleic acid encoding the chondroitin synthase according to any one of (1) to (3).

(5) An expression vector which comprises the nucleic acid according to (4).

(6) The expression vector according to (5), which is capable of being expressed in a eucaryotic cell.

(7) A transformant which comprises the expression vector according to (5) or (6).

(8) A process for producing a chondroitin synthase, which comprises growing the transformant according to (7) to produce and accumulate a chondroitin synthase as a grown material, and recovering the chondroitin synthase from the grown material.

(9) A method for synthesizing a sugar chain having a structure represented by the following formula (2), which comprises allowing the chondroitin synthase according to any one of (1) to (3) to act on an N-acetyl-D-galactosamine acceptor having a structure represented by the following formula (1) and an N-acetyl-D-galactosamine donor to thereby transfer an N-acetyl-D-galactosamine residue to the N-acetyl-D-galactosamine acceptor:

wherein, in formulae (1) and (2), GalNAc represents the N-acetyl-D-galactosamine residue; GlcUA represents a D-glucuronic acid residue; n is an integer of 1 or more; m is 1 or 0; and - represents a glycoside bond.

(10) A method for synthesizing a sugar chain having a structure represented by the following formula (4), which comprises allowing the chondroitin synthase according to any one of (1) to (3) to act upon a D-glucuronic acid acceptor having a structure represented by the following formula (3) and a D-glucuronic acid donor to thereby transfer a D-glucuronic acid residue to the D-glucuronic acid acceptor:

(GalNAc-GlcUA)$_n$-(GalNAc)$_m$    (3)

GlcUA-(GalNAc-GlcUA)$_n$-(GalNAc)$_m$    (4)

wherein, in formulae (3) and (4), GalNAc represents an N-acetyl-D-galactosamine residue; GlcUA represents the D-glucuronic acid residue; n is an integer of 1 or more; m is 1 or 0; and - represents a glycoside bond.

(11) Use of the chondroitin synthase according to any one of (1) to (3) for synthesis of a sugar chain having a structure represented by the following formula (2) by transferring an N-acetyl-D-galactosamine residue to a D-glucuronic acid residue which is present at the non-reducing end of an N-acetyl-D-galactosamine acceptor having a structure represented by the following formula (1):

(GlcUA-GalNAc)$_n$-(GlcUA)$_m$    (1)

GalNAc-(GlcUA-GalNAc)$_n$-(GlcUA)$_m$    (2)

wherein, in formulae (1) and (2), GalNAc represents the N-acetyl-D-galactosamine residue; GlcUA represents a D-glucuronic acid residue; n is an integer of 1 or more; m is 1 or 0; and - represents a glycoside bond.

(12) Use of the chondroitin synthase according to any one of (1) to (3) for synthesis of a sugar chain having a structure represented by the following formula (4) by transferring a D-glucuronic acid residue to an N-acetyl-D-galactosamine residue which is present at the non-reducing end of a D-glucuronic acid acceptor having a structure represented by the following formula (3):

(GalNAc-GlcUA)$_n$-(GalNAc)$_m$    (3)

GlcUA-(GalNAc-GlcUA)$_n$-(GalNAc)$_m$    (4)

wherein, in formulae (3) and (4), GalNAc represents an N-acetyl-D-galactosamine residue; GlcUA represents the D-glucuronic acid residue; n is an integer of 1 or more; m is 1 or 0; and - represents a glycoside bond.

(13) An activity-controlling agent of the chondroitin synthase according to any one of (1) to (3).

(14) An agent for treating diseases caused by a change in activity of the chondroitin synthase according to any one of (1) to (3), which comprises the activity-controlling agent according to (13) as an active ingredient.

BEST MODE FOR CARRYING OUT THE INVENTION

Figure 1:
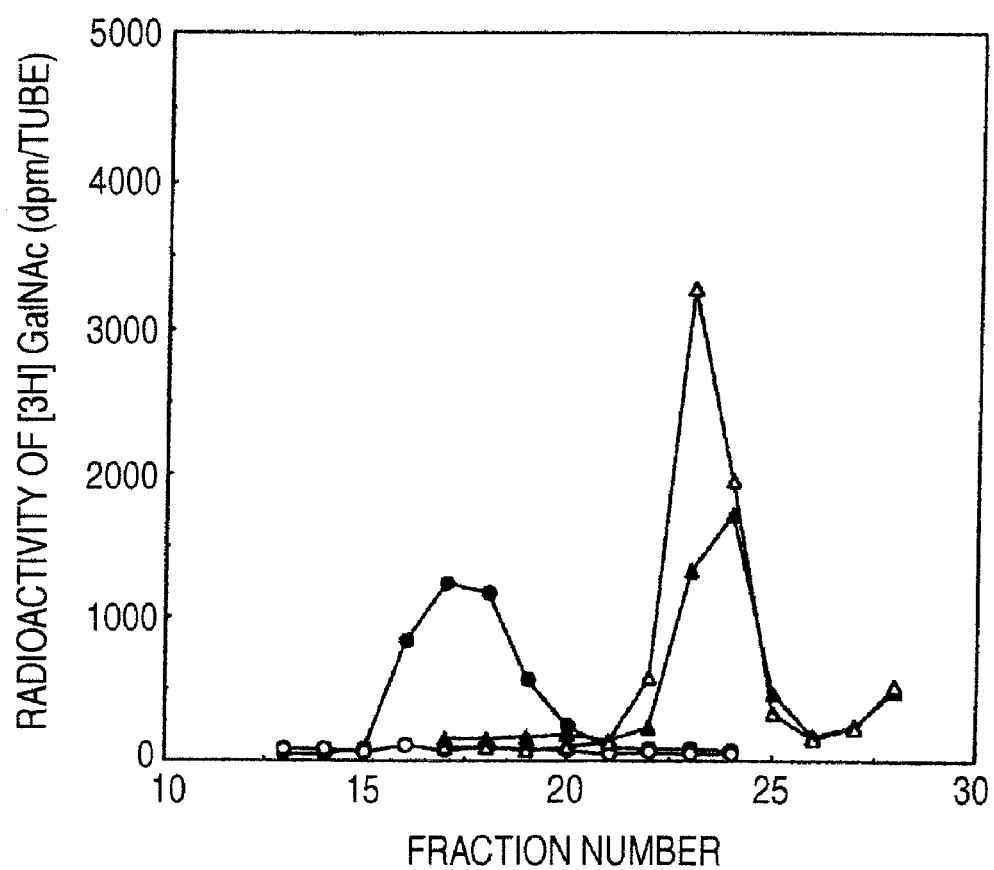
FIG. 1 is a graph showing a chromatography chart which shows synthesis of odd-numbered saccharides by the GalNAc transfer activity of the enzyme of the present invention. Open circles represent a chart showing the GalNAc transfer activity upon chondroitin sulfate, closed circles represent chart showing the GalNAc transfer activity upon chondroitin, open triangles represent a chart showing the GalNAc transfer activity upon chondroitin sulfate deca-saccharide, and closed triangles represent a chart showing the GalNAc transfer activity upon chondroitin deca-saccharide.

In order to solve the above-described problems, the present inventors have conducted intensive studies, and found, as a result, that there is a different enzyme having an enzyme activity similar to that of the conventionally known chondroitin synthase. Thereafter, the present invention has been accomplished by obtaining a DNA for the enzyme and preparing the enzyme.

The present invention is described below in detail based on the embodiments of the present invention.

(1) Enzyme of the Present Invention

The enzyme of the present invention is a chondroitin synthase which consists of a polypeptide consisting of the amino acid sequence represented by SEQ ID NO:2 or an amino acid sequence consisting of amino acid numbers 130 to 882 in the amino acid sequence represented by SEQ ID NO:2, or a sugar chain-bound polypeptide in which a sugar chain is bound to the polypeptide.

The enzyme of the present invention has activity of transferring GalNAc and activity of transferring GlcUA (the activity of transferring GalNAc is referred to as "GalNAc transferring activity", and the activity of transferring GlcUA is referred to as "GlcUA transferring activity") to sugar residues which are present at the non-reducing end of the chondroitin backbone. That is, the enzyme of the present invention shows the activity of transferring GalNAc to a GlcUA residue when the GlcUA residue is present at the non-reducing end of the chondroitin backbone, and shows the activity of transferring GlcUA to a GalNAc residue when the GalNAc residue is present at the non-reducing end. This is because such an enzyme has the most valuable in synthesizing the chondroitin backbone.

Accordingly, it is preferred that the enzyme of the present invention uses both of a GalNAc acceptor having a GlcUA residue at the non-reducing end of the chondroitin backbone and a GlcUA acceptor having a GalNAc residue at the non-reducing end, as the sugar residue acceptors.

The GalNAc acceptor of the enzyme of the present invention comprises, for example, a structure represented by the following formula (1):

$$(GlcUA\text{-}GalNAc)_n\text{-}(GlcUA)_m \quad (1)$$

In formula (1), GlcUA represents a D-glucuronic acid residue; GalNAc represents an N-acetyl-D-galactosamine residue; n is an integer of 1 or more; m is 1 or 0; and - represents a glycoside bond. In the GalNAc acceptor, the above-described n is preferably 2 or more, and more preferably 4 or more. This is because the chondroitin backbone can be efficiently elongated when it is within such a range.

Examples of the GalNAc acceptor having the structure of formula (1) include chondroitin, chondroitin sulfate, and a molecular weight-lowered chondroitin or chondroitin sulfate obtained by digesting them, although not limited thereto.

The enzyme of the present invention transfers a GalNAc residue from a GalNAc donor to the GalNAc acceptor having the structure of formula (1). Since the enzyme of the present invention is useful in synthesizing the chondroitin backbone, it is preferred that the GalNAc residue is transferred to a GlcUA residue at the non-reducing end through a β1,4-glycoside bond.

The GalNAc donor is preferably a sugar nucleotide having the GalNAc residue. Examples of such a substance include adenosine diphosphate-N-acetylgalactosamine (ADP-GalNAc), uridine diphosphate-N-acetylgalactosamine (UDP-GalNAc), guanosine diphosphate-N-acetylgalactosamine (GDP-GalNAc), cytidine diphosphate-N-acetylgalactosamine (CDP-GalNAc) and the like, and UDP-GalNAc is most preferred. This is because UDP-GalNAc mainly acts as a GalNAc donor in the in vivo synthesis of the chondroitin backbone. However, regarding the GalNAc transferring activity by the enzyme of the present invention, the GalNAc donor is not particularly limited, so long as it can provide a GalNAc residue.

A sugar chain having a structure represented by the following formula (2) is obtained when a GalNAc residue is transferred by the enzyme of the present invention to a GalNAc acceptor having a structure represented by the above-described formula (1):

$$GalNAc\text{-}(GlcUA\text{-}GalNAc)_n\text{-}(GlcUA)_m \quad (2)$$

In formula (2), GlcUA, GalNAc, n, m and - have the same meanings as described above.

The GalNAc acceptor has a structure represented by the above-described formula (1), and a substance having a structure in which a sugar chain, a protein, a lipid, a synthetic high molecular weight compound or the like is further bound thereto can also be used as a GalNAc acceptor. When a GalNAc residue is transferred to the GalNAc acceptor, a compound having a structure represented by the above-described formula (2) and also having a sugar chain, a protein, a lipid, a synthetic high molecular weight compound or the like at the reducing end is obtained.

The GalNAc transferring activity of the enzyme of the present invention can be easily detected and measured by using a technique in which GalNAc is labeled with a radioisotope like the method described in Example 2(1) of this specification.

The GlcUA acceptor of the enzyme of the present invention comprises, for example, a structure represented by the following formula (3):

$$(GalNAc\text{-}GlcUA)_n\text{-}(GalNAc)_m \quad (3)$$

In formula (1), GlcUA represents a D-glucuronic acid residue; GalNAc represents N-acetyl-D-galactosamine residue; n is an integer of 1 or more; m is 1 or 0; and - represents a glycoside bond. In the GlcUA acceptor, the above-described n is preferably 2 or more, and more preferably 4 or more. This is because the chondroitin backbone can be efficiently elongated when it is within such a range.

Examples of the GlcUA acceptor having the structure of formula (3) include chondroitin, chondroitin sulfate, or lower molecular weight chondroitin or chondroitin sulfate which is obtainable by cleaving them, although the present invention is not limited thereto.

The enzyme of the present invention transfers a GlcUA residue from a GlcUA donor substrate to the GlcUA acceptor having the structure represented by formula (3). Since the enzyme of the present invention is useful in synthesizing the chondroitin backbone, it is preferred that the GlcUA residue is transferred to the GalNAc residue through a β1,3 glycoside bond.

The GlcUA donor is preferably a sugar nucleotide having a GlcUA residue. Examples of such a substance include adenosine diphosphate-N-glucuronic acid (ADP-GlcUA), uridine diphosphate-N-glucuronic acid (UDP-GlcUA), guanosine diphosphate-N-glucuronic acid (GDP-GlcUA), cytidine diphosphate-N-glucuronic acid (CDP-GlcUA) and the like, and UDP-GlcUA is most preferable. This is because UDP-GlcUA mainly acts as a GlcUA donor in the in vivo synthesis of the chondroitin backbone. However, regarding GlcUA transferring activity by the enzyme of the present invention, the GlcUA donor is not particularly limited, so long as it can provide the GlcUA residue.

A sugar chain having a structure of the following formula (4) is obtained when a GlcUA residue is transferred by the enzyme of the present invention to a GlcUA acceptor having a structure represented by the above-described formula (3):

$$GlcUA\text{-}(GalNAc\text{-}GlcUA)_n\text{-}(GalNAc)_m \quad (4)$$

In formula (4), GlcUA, GalNAc, n, m and - have the same meanings as described above.

Also, the GlcUA acceptor has a structure represented by the above-described formula (3), and a substance having a structure in which a sugar chain, a protein, a lipid, a synthetic high molecular weight compound or the like is further bound thereto can also be used as a GlcUA acceptor. When a GlcUA residue is transferred to such a GlcUA acceptor, a compound having a structure represented by the above-described formula (4) and also having a sugar chain, a protein, a lipid, a synthetic high molecular weight compound or the like at the reducing end is obtained.

The GlcUA transferring activity of the enzyme of the present invention can be easily measured by using a technique in which GlcUA is labeled with a radioisotope like the method described in Example 2(2) of this specification.

Preferably, the enzyme of the present invention comprises a polypeptide consisting of an amino acid sequence consisting of amino acid numbers 130 to 882 in the amino acid sequence represented by SEQ ID NO:2. This is because a polypeptide comprising an amino acid sequence of such a range has both of the above-described GalNAc transferring activity and GlcUA transferring activity (cf. Example 2 of this specification).

In general, the activity of an enzyme is maintained even when its constituting protein has a few substitution, deletion, insertion, addition and/or transposition of amino acids (hereinafter generally referred to as "amino acid mutation"), and an enzyme having such an amino acid mutation is called variant. In general, the enzyme activity is sufficiently maintained when the amino acid mutation is about 20% of the total number of amino acids, so long as it is not a mutation relating to the active center. Accordingly, so long as it has the above-described GalNAc transferring activity and GlcUA transferring activity, the enzyme of the present invention may also have a few amino acid mutation in the amino acid sequence consisting of amino acid numbers 130 to 882 in the amino acid sequence represented by SEQ ID NO:2 (it is possible to examine the presence or absence of the enzyme activity in accordance with Example 2 of this specification as described above). Also, the above-described "a few" is 20% or less of the total number of amino acids constituting the enzyme (150 or less in the case of the polypeptide consisting of amino acid numbers 130 to 882 in SEQ ID NO:2, namely a homology of 80% or more), preferably 15% or less (112 or less in the case of the polypeptide consisting of amino acid numbers 130 to 882 in SEQ ID NO:2, namely a homology of 85% or more), and most preferably 10% or less (75 or less in the case of the polypeptide consisting of amino acid numbers 130 to 882 in SEQ ID NO:2, namely a homology of 90% or more). The homology of the amino acid sequences can be easily calculated by using conventionally known computer software such as FASTA. The computer software such as FASTA is also served by internet.

Furthermore, it can be said that an enzyme constituted by a polypeptide consisting of the complete sequence of the amino acid sequence represented by SEQ ID NO:2 is also constituted by a polypeptide obtained through a few mutation generated in the polypeptide consisting of amino acid numbers 130 to 882, and it can be said that this is within the range of a preferable polypeptide as the enzyme of the present invention.

In addition, there are many mammal-derived proteins to which sugar chains are bound, and both of the enzyme consisting of the polypeptide alone and the enzyme in which sugar chain is bound to the polypeptide are included in the enzyme of the present invention.

Also, it is preferred that the enzyme of the present invention has the following properties.

Increase of the Activity:

The activity is increased when 10 mmol/l of a divalent metal cation (preferably manganese ion or cobalt ion) is present in the reaction system. Specifically, a halide (such as chloride) of the above metal cation may be present in the reaction system.

Inhibition of the Activity:

The enzyme activity is substantially lost when 10 mmol/l in concentration of ethylenediaminetetraacetic acid is present in the reaction system.

Optimum Reaction pH:

The GlcUA transferring enzyme activity is from pH 5.7 to 6.7, preferably from pH 6.0 to 6.5, in a 2-morpholinoethanesulfonate (MES) buffer, and the GalNAc transferring enzyme activity is from pH 5.7 to 6.7, preferably from pH 6.0 to 6.4, in an MES buffer.

In addition, by making use of an activity measuring system of the enzyme of the present invention, a substance having activity of accelerating or inhibiting the enzyme activity can be obtained through its screening. It is possible to use such a substance as the active ingredient of an activity-controlling agent for the enzyme of the present invention. Furthermore, the activity-controlling agent can be used as an agent for treating diseases caused by a change in activity of the enzyme of the present invention.

(2) Nucleic Acid of the Present Invention

The nucleic acid of the present invention is characterized in that it encodes the enzyme of the present invention.

That is, the nucleic acid of the present invention is not particularly limited, so long as the enzyme of the present invention can be produced by expression in a transformant transformed with an expression vector containing the nucleic acid or nucleic acid having a nucleotide sequence complementary thereto. Also, the nucleic acid of the present invention may be either a DNA or an RNA, but a DNA is preferred since it is markedly excellent in stability.

The preferred embodiments of the nucleic acid of the present invention include a DNA consisting of nucleotide numbers 388 to 2649 in the nucleotide sequence represented by SEQ ID NO:1, and a DNA consisting of the complete nucleotide sequence represented by SEQ ID NO:1.

By the way, in the biosynthesis of a protein, the genetic code (triplet) and the amino acid is not always 1:1, and there are cases in which the same amino acid corresponds to different triplets (degeneracy of genetic code). Accordingly, it can be easily understood by those skilled in the art that nucleic acid other than the exemplified specific nucleotide sequence, which contains other triplet corresponding to the same amino acid due to the degeneracy of genetic code, can also be used for obtaining the same enzyme of the present invention as a result, and it goes without saying that such nucleic acid is included in the nucleic acid of the present invention.

Nucleic acid which hybridizes with a DNA consisting of the nucleotide numbers 388 to 2649 in the nucleotide sequence represented by SEQ ID NO:1 or a DNA consisting of a nucleotide sequence complementary thereto under stringent conditions can be used, for example, as a probe for inspecting in vivo expression state and the like of the nucleic acid of the present invention, and is markedly useful as a reagent. Since the nucleic acid as a probe becomes difficult to handle when its molecular weight is too large, the molecular weight is, for example, 500 bp to 10 kbp, more preferably from 600 bp to 9 kbp, and most preferably from 700 bp to 8 kbp.

In this connection, the stringent conditions as used herein include conditions used in general hybridization techniques (e.g., Northern blot hybridization and Southern blot hybridization), and preferred conditions are conditions at 42° C. in the presence of 37.5% formamide, 5×SSPE (sodium chloride/sodium phosphate/EDTA (ethylenediaminetetraacetic acid) buffer), 5×Denhardt's solution and 0.5% SDS (sodium dodecyl sulfate).

(3) Expression Vector of the Present Invention

The expression vector of the present invention is an expression vector which comprises the nucleic acid of the present invention. In the expression vector of the present invention, regions relating to the gene expression (promoter region, enhancer region, operator region, etc.) are appropriately arranged so that the above-described nucleic acid of the present invention can be expressed in a host cell of interest, and the vector is constructed in such a manner that the nucleic acid of the present invention can be expressed suitably. Accordingly, a transformat can be obtained by introducing the expression vector of the present invention into an appropriate host cell. A basal vector of the expression vector of the present invention (a vector before transferring the gene of the present invention) is optionally selected in relation to the host cell into which the expression vector is introduced. For example, a vector for eucaryotic cell is selected as the basal vector when a eucaryotic cell (mammal cell, yeast, insect cell, etc.) is used as the host cell, and a vector for procaryotic cell is selected as the basal vector when a procaryotic cell (*Escherichia coli*, *Bacillus subtilis*, etc.) is used as the host cell. By the way, since the enzyme of the present invention is an enzyme derived from human, it is considered that an enzyme of the present invention having properties close to the natural counterpart (e.g., sugar chain-added embodiment, etc.) can be obtained when a eucaryotic cell is used in the present invention as the host cell. Accordingly, a eucaryotic cell, particularly a mammal cell, is preferably selected as the host cell, and a vector for eucaryotic cell, particularly a vector for mammal cell, is preferably selected as the basal vector of the expression vector of the present invention.

In this connection, techniques have been established in recent years as genetic engineering techniques in which a transformant is cultured or grown, and the substance of interest is isolated and purified from the culture or the grown material. It is preferable to construct the expression vector of the present invention in such a manner that isolation and purification of the enzyme of the present invention become easy. Particularly, it is preferable to prepare the enzyme of the present invention by means of genetic engineering using the vector of the present invention constructed in such a manner that the enzyme of the present invention is expressed as a fusion protein with a marker peptide, because its isolation, purification and detection become relatively easy.

Examples of the above-described marker peptide include a peptide which makes secretion, isolation, purification or detection of the protein of interest from the grown material of a transformant easy, by expressing as a fusion protein in which the peptide is bound to the protein of interest, in preparing the protein of interest through genetic recombination. Examples of the marker peptide include peptides such as a signal peptide (peptide consisting of 15 to 30 amino acid residues, which is present at the N-terminus of various proteins and functions inside the cells in the intracellular membrane permeation mechanism for the selection of protein; e.g., OmpA, OmpT, Dsb, etc.), protein kinase A, protein A (protein as a constituting component of the cell wall of *Staphylococcus aureus*, having a molecular weight of about 42,000), glutathione S transferase, His tag (sequence in which 6 to 10 histidine residues are arranged), myc tag (cMyc protein-derived sequence of 13 amino acid residues), FLAG peptide (a marker for analysis, consisting of 8 amino acid residues), T7 tag (consisting of the first 11 amino acid residues of gene 10 protein), S tag (consisting of 15 amino acid residues derived from pancreatic RNase A), HSV tag, pelB (a sequence of 22 amino acid residues of *Escherichia coli* outer membrane protein pelB), HA tag (consisting of 10 amino acid residues derived from hemagglutinin), Trx tag (thioredoxin sequence), CBP tag (calmodulin binding peptide), CBD tag (cellulose binding domain), CBR tag (collagen binding domain), β-lac/blu (β-lactamase), β-gal (β-galactosidase), luc (luciferase), HP-Thio (His-patch thioredoxin), HSP (heat shock peptide), Lnγ (laminin γ peptide), Fn (fibronectin partial peptide), GFP (green fluorescent peptide), YFP (yellow fluorescent peptide), CFP (cyan fluorescent peptide), BFP (blue fluorescent peptide), DsRed, DsRed2 (red fluorescent peptide), MBP (maltose binding peptide), LacZ (lactose operator), IgG (immunoglobulin G), avidin, and protein G, and any one of these marker peptides can be used. Among these, a signal peptide, protein kinase A, protein A, glutathione S transferase, His tag, myc tag, FLAG peptide, T7 tag, S tag, HSV tag, pelB or HA tag is preferred since it facilitates expression of the substance of the present invention by means of genetic engineering techniques and its purification, and it is particularly preferable to prepare the enzyme of the present invention as a fusion protein with FLAG peptide because of the markedly excellent handling.

Examples of the basal vector which can be expressed in mammal cells and can provide the enzyme of the present invention as a fusion protein with the above-described FLAG peptide include pFLAG-CMV-1 (manufactured by Sigma) and the like, but it is possible for those skilled in the art to select a suitable basal vector by judging from the host cell, the restriction enzyme, the marker peptide and the like used in the expression of the enzyme of the present invention.

(4) Processes for Preparing the Nucleic Acid of the Present Invention, the Expression Vector of the Present Invention and the Transformant Since the nucleotide sequence of the nucleic acid of the present invention has been disclosed by the present invention, it is possible for those skilled in the art to prepare optional primers based on the nucleotide sequences of both termini of a region of the nucleic acid of the present invention of interest or nucleic acid to be prepared, and to prepare the region of interest by amplifying it by PCR or the like using the primers. A DNA consisting of nucleotide numbers 388 to 2649 of SEQ ID NO:1 as a preferred embodiment of the nucleic acid of the present invention can be prepared as follows.

A partial sequence of the nucleic acid of the present invention can be obtained by carrying out BLAST search using the amino acid sequence of a known β1,4-galactosyltransferase (β4Gal-T) (amino acid sequence encoded by GenBank accession No. D29805) as a query. Thereafter, the genomic sequence can be searched from a data base, for example, based on the EST obtained thereby (GenBank accession No. AC004219, etc.). The genomic sequence can be searched by using, for example, GenScan (Stanford University, USA) or the like. The total nucleotide sequence represented by SEQ ID NO:1 can be obtained by this method. The DNA consisting of nucleotide numbers 388 to 2649 can be prepared by preparing primers from the nucleotide sequence obtained in this manner. As the preparation method of DNA, for example, a polymerase chain reaction method (hereinafter referred to as "PCR method") can be preferably cited. In the PCR method, it is preferred that appropriate restriction enzyme sites are contained in respective primers in advance corresponding to a vector, for facilitating introduction of the nucleic acid of the present invention into the vector. Examples of the primers include the nucleotide sequence represented by SEQ ID NO:3 (containing HindIII site) as a 5' primer, and the nucleotide sequence represented by SEQ ID NO:4 (containing XbaI site) as a 3' primer.

For example, it can be found from the information of a data base that the genome obtained by the search based on the EST of GenBank accession No. AC004219 by GenScan is expressed in the human brain. Accordingly, a commercially available human brain cDNA library (e.g., Marathon-Ready cDNA human brain (manufactured by Clontech, etc.)) or the like can be used as the template of the PCR method.

When the PCR method is carried out by using the primers exemplified above, the nucleic acid of the present invention (DNA) is formed as an amplified product of about 2.3 kb. The amplified product can be isolated in accordance with the usual methods, for example, separation of DNA based on molecular weight such as agarose gel electrophoresis, cutting out of the gel, and extraction of the nucleic acid of the present invention.

Since the primers exemplified above contains HindIII site and XbaI site, insertion into a vector having HindIII and XbaI sites can be carried out in the usual way by treating with these restriction enzymes. For example, since the pFLAG-CMV-1 as a basal vector exemplified above contains HindIII and XbaI sites, the vector of the present invention can be obtained by digesting this basal vector with HindIII and XbaI and ligating it with the nucleic acid of the present invention.

The vector of the present invention can be introduced into a host cell in accordance with a usual method. When pFLAG-CMV-1 is used as the basal vector, a transformant can be obtained by introducing it into a mammal-derived cell, such as COS1 cell or COS7 cell, which functions as a host cell of pFLAG-CMV-1, according to a usual method such as electroporation.

(5) Preparation Method of the Enzyme of the Present Invention

The preparation method of the enzyme of the present invention is characterized in that the transformant of the present invention is grown, the enzyme of the present invention is produced and accumulated in the grown material, and then the above-described enzyme of the present invention is isolated from the grown material.

The enzyme of the present invention can be prepared by growing a transformant under conditions suitable for its growth, expressing the nucleic acid of the present invention, and then preparing the product from the grown material.

In this case, the growth of a host cell is a general idea which includes not only culturing of the host cell but also administration of the host cell to a living body or the like and subsequent in vivo growth of the host cell. In addition, the grown material is a general idea which includes not only cultured host cell and culture supernatant but also, when the host cell is grown in vivo, discharged substances, secreted substances and the like from the living body.

For example, when COS-7 cell is selected as the host cell, it is possible to culture the transformant in vitro and to purify the substance of the present invention from its cultured material (transformant and culture supernatant after its culturing).

As the method for isolating and purifying the enzyme of the present invention, it is possible to select an appropriate method optionally and conventionally, depending on the marker peptide. Particularly, when the above-described pFLAG-CMV-1 vector is used, the enzyme of the present invention is obtained as a fusion protein with FLAG peptide, so that it is possible to isolate and purify the enzyme of the present invention from the substance of the present invention by a method such as affinity purification, for example, using an anti-FLAG antibody (e.g., M1, etc.). When a resin or the like to which an anti-FLAG antibody is bound is used, it is possible to easily isolate and purify the protein from cultured materials of the host cell (culture supernatant, extracts of the host cell, etc.), and it is also possible to use the resin as an enzyme suspension by directly suspending it in a buffer or the like.

(6) Synthesis Method of the Present Invention (a) Synthesis Method 1 of the Present Invention The synthesis method 1 of the present invention is a method for synthesizing a sugar chain having a structure represented by the following formula (2), characterized in that the enzyme of the present invention is allowed to act upon a GalNAc acceptor having a structure represented by the following formula (1) and a GalNAc donor to thereby transfer a GalNAc residue from the GalNAc donor to the GalNAc acceptor:

(GlcUA-GalNAc)$_n$-(GlcUA)$_m$ (1)

GalNAc-(GlcUA-GalNAc)$_n$-(GlcUA)$_m$ (2)

In formulae (1) and (2), GalNAc represents an N-acetyl-D-galactosamine residue; GlcUA represents a D-glucuronic acid residue; n is an integer of 1 or more; m is 1 or 0; and - represents a glycoside bond.

According to the synthesis method 1 of the present invention, the GalNAc acceptor is not particularly limited, so long as it has a sugar chain of the above-described formula (1) as a subject to which the GalNAc residue is transferred, GlcUA transferring enzyme activity and it may be a material having a structure in which a sugar chain, a protein, a lipid, a synthetic high molecular weight compound or the like is further bound to its reducing end.

When the GalNAc residue is transferred from a GalNAc donor by allowing the enzyme of the present invention to act upon the GalNAc acceptor of the above-described formula (1), a compound having a structure represented by the above-described formula (2) is obtained.

The chondroitin backbone consists of a structure in which a disaccharide obtained by the GlcUA residue and the GalNAc residue though a β1,3-glycoside bond is further bound through a β1,4-glycoside bond, and it is preferred that the GalNAc residue can be bound to such a sugar chain also in the case of the synthesis method 1 of the present invention. That is, it is more preferable that the GalNAc acceptor having the structure of the above-described formula (1) has a structure of the following formula (1'):

(4GlcUAβ1-3GalNAcβ1)$_n$-4(GlcUA)$_m$ (1')

In formula (1'), GlcUA, GalNAc and - have the same meanings as those described in the above-described formula (1); β represents a β bond; and the numerals indicate binding positions of adjoining sugar residues (positions on which a glycoside bond is present).

A product comprising a structure of the following formula (2') is preferably obtained by transferring a GalNAc residue to formula (1') by the enzyme of the present invention. This is because the activity of binding the GalNAc residue to the GlcUA residue through a β1,4 glycoside bond is necessary for the synthesis of the chondroitin backbone:

$$GalNAc\beta 1\text{-}(4GlcUA\beta 1\text{-}3GalNAc\beta 1)_n\text{-}4(GlcUA)_m \qquad (2')$$

In formula (2'), GlcUA, GalNAc and - have the same meanings as those described in the above-described formula (2); β represents a β bond; and the numerals indicate binding positions of adjoining sugar residues (positions on which a glycoside bond is present).

According to the synthesis method 1 of the present invention, the GalNAc residue is transferred from a GalNAc donor to a GalNAc acceptor. The enzyme of the present invention used in the synthesis method 1 of the present invention is preferably one which transfers the GalNAc residue from the above-described GalNAc donor to the above-described GalNAc acceptor through a β1,4 glycoside bond. This is because the GalNAc residue is bound to the chondroitin backbone through a β1,4 glycoside bond.

The transfer reaction of the GalNAc residue from a GalNAc donor to a GalNAc acceptor in the synthesis method of the present invention is preferably carried out within the range of the optimum reaction pH and optimum reaction temperature of the enzyme of the present invention. For example, the pH is preferably from 5.0 to 9.0, more preferably from 5.3 to 8.0, most preferably from 5.7 to 7.5, and still most preferably from 6.0 to 7.0. In order to maintain such conditions, the above-described transfer reaction is preferably carried out in a buffer. Examples of the buffer include an acetate buffer, an MES buffer, a hydroxymethylaminoethane-hydrochloric acid buffer (hereinafter sometimes simply referred to as "Tris-HCl buffer"), an imidazole buffer, a sodium phosphate buffer and the like, and any one of them can be used. However, MES is most preferred because of its potent activity to keep the pH stable throughout the most preferable pH range (pH 6.0 to 7.0) according to the synthesis method of the present invention. Although the concentration of buffer agents of the buffer is not particularly limited, a range of from 10 to 200 mol/l, from 20 to 100 mmol/l as a preferred range, can be exemplified.

In addition, it is preferred that a divalent metal cation, more preferably a manganese ion, a cobalt ion, a cadmium ion, or the like, most preferably a manganese ion, is contained in this buffer for the purpose of accelerating the enzyme activity. The metal cation may be added in the form of a salt to the buffer. Examples of the salt include a halide of the above-described metal cation such as manganese chloride. Furthermore, the buffer preferably contains adenosine triphosphate (hereinafter also referred to as "ATP").

The temperature at the time of the reaction is, for example, from 20 to 45° C., preferably from 24 to 40° C., and more preferably from 36 to 37° C.

The enzyme of the present invention can be used in the synthesis of the sugar chains described in the above-described formula (2) and formula (2'), and its use for transferring the GalNAc residue which is present at the non-reducing end of a sugar chain having a structure of formula (2) or formula (2') is regarded as the use of the present invention.

(b) Synthesis Method 2 of the Present Invention

The synthesis method 2 of the present invention is a method for synthesizing a sugar chain having a structure represented by the following formula (4), characterized in that the enzyme of the present invention is allowed to act upon a GlcUA acceptor having a structure represented by the following formula (3) and a GlcUA donor to thereby transfer a GlcUA residue from the GlcUA donor to the GlcUA acceptor:

$$(GalNAc\text{-}GlcUA)_n\text{-}(GalNAc)_m \qquad (3)$$

$$GlcUA\text{-}(GalNAc\text{-}GlcUA)_n\text{-}(GalNAc)_m \qquad (4)$$

In formulae (3) and (4), GalNAc represents an N-acetyl-D-galactosamine residue; GlcUA represents a D-glucuronic acid residue; n is an integer of 1 or more; m is 1 or 0; and - represents a glycoside bond.

According to the synthesis method 2 of the present invention, the GlcUA acceptor is not particularly limited, so long as it has a sugar chain of the above-described formula (3) as a subject to which a GlcUA residue is transferred, and it may be a material having a structure in which a sugar chain, a protein, a lipid, a synthetic high molecular weight compound or the like is further bound to its reducing end.

When the GlcUA residue is transferred from a GlcUA donor by allowing the enzyme of the present invention to act upon the GlcUA acceptor of the above-described formula (3), a compound having a structure represented by the above-described formula (4) is obtained.

The chondroitin backbone consists of a structure in which a disaccharide obtained by the GlcUA residue and the GalNAc residue through a β1,3 glycoside bond is further bound through a β1,4 glycoside bond, and it is preferable that GlcUA residue can be bound to such a sugar chain also in the synthesis method 2 of the present invention similar to the case of the synthesis method 1 of the present invention. That is, more preferably, the GlcUA acceptor having the structure of the above-described formula (3) has a structure of the following formula (3'):

$$(3GalNAc\beta 1\text{-}4GlcUA\beta 1)_n\text{-}3(GalNAc)_m \qquad (3')$$

In formula (3'), GlcUA, GalNAc and - have the same meanings as those described in the above-described formula (3); β represents a β bond; and the numerals indicate binding positions of adjoining sugar residues (positions on which a glycoside bond is present).

A product comprising a structure of the following formula (4') is preferably obtained by transferring the GlcUA residue to formula (3') by the enzyme of the present invention. This is because activity of binding the GlcUA residue to the GalNAc residue through a β1,3 glycoside bond is necessary for the synthesis of the chondroitin backbone:

$$GlcUA\beta 1\text{-}(3GalNAc\beta 1\text{-}4GlcUA\beta 1)_n\text{-}3(GalNAc)_m \qquad (4')$$

In formulae (3') and (4'), GlcUA, GalNAc and - have the same meanings as those described in the above-described formulae (1) and (2); β represents a β bond; and the numerals indicate binding positions of adjoining sugar residues (positions on which a glycoside bond is present).

According to the synthesis method 2 of the present invention, the GlcUA residue is transferred from a GlcUA donor to a GlcUA acceptor. The enzyme of the present invention used in the synthesis method 2 of the present invention is preferably one which transfers the GlcUA residue from the above-described GlcUA donor to the above-described GlcUA acceptor through a β1,3 glycoside bond. This is because the GlcUA residue is bound to the chondroitin backbone through a β1,3 glycoside bond.

The transfer reaction of the GlcUA residue from a GlcUA donor to a GlcUA acceptor in the synthesis method of the present invention is preferably carried out at the optimum reaction pH and optimum reaction temperature of the enzyme of the present invention. For example, the pH is preferably from 4.0 to 8.0, more preferably from 4.5 to 7.0, and most preferably from 5.0 to 6.5. In order to maintain such conditions, the above-described transfer reaction is preferably carried out in a buffer. Examples of the buffer include an acetate buffer, MES, a Tris-HCl buffer, a sodium phosphate buffer and the like, and any one of them can be used. However, an acetate buffer and MES are preferred and MES is most preferred because of its potent activity to keep the pH stable throughout the most preferred pH range (pH 5.0 to 5.5) according to the synthesis method of the present invention. This is because the pH can be kept more stably since pH 5.0 to 6.5 is a center range among the buffering region. Although the concentration of buffer agents of the buffer is not particularly limited, a range of from 10 to 200 mol/l, from 20 to 100 mmol/l as a preferred range, can be exemplified.

In addition, a divalent metal cation, more preferably a manganese ion, a cobalt ion, a cadmium ion, or the like, and most preferably a manganese ion, is contained in this buffer for the purpose of accelerating the enzyme activity. The metal cation may be added in the form of a salt to the buffer. Examples of the salt include a halide of the above-described metal cation such as manganese chloride.

The temperature at the time of the reaction is, for example, from 20 to 45° C., preferably from 24 to 40° C., and most preferably from 36 to 37° C.

The enzyme of the present invention can be used in the synthesis of the sugar chains described in the above-described formula (4) and formula (4'), and its use for transferring GlcUA residue existing at the non-reducing end of a sugar chain having a structure of formula (4) or formula (4') is regarded as the use of the present invention.

EXAMPLE 1

Preparation of Enzyme of the Present Invention (1) Cloning of cDNA and Construction of Expression Vector BLAST search was carried out by using an amino acid sequence of β1,4-galactosyltransferase (β4Gal-T) (the amino acid sequence encoded by GenBank accession No. D29805) as the query. As a result, EST (GenBank accession No. AC0004219) was found. However, since this sequence was incomplete, ORF was examined from a genomic data base by GenScan (Stanford University, USA). As a result, the nucleotide sequence represented by SEQ ID NO:1 (the encoded amino acid sequence in SEQ ID NO:2) was found. It was confirmed by RT-PCR using Marathon-Ready cDNA (manufactured by Clontech) as the template that a gene consisting of the nucleotide sequence represented by SEQ ID NO:1 was expressed at least in the human brain (As primers for PCT, SEQ ID NO:5 and SEQ ID NO:6, and SEQ ID NO:7 and SEQ ID NO:8 which are combinations of 5'-primer and 3'-primer are used). In order to carry out cloning of the soluble region of this gene except for a region including the transmembrane region (a region consisting of amino acid numbers 1 to 129 of SEQ ID NO:2), PCR was carried out in accordance with a usual method by using two primers represented by SEQ ID NO:3 and SEQ ID NO:4. As the template cDNA used, Marathon-Ready cDNA human brain (manufactured by Clontech) was used. The thus amplified band of about 2.3 kb was digested with HindIII and XbaI in accordance with a usual method and inserted into HindIII and XbaI sites of an expression vector for mammal cell, pFLAG-CMV-1 (manufactured by Sigma), to thereby obtain the vector of the present invention (K3-FLAG-CMV1). As a result that the nucleotide sequence of the thus obtained vector was confirmed, it was confirmed that a DNA fragment consisting of nucleotide numbers 388 to 2649 of the nucleotide sequence represented by SEQ ID NO:1 was inserted.

(2) Preparation of the Enzyme of the Present Invention

Using 15 μg of the K3-FLAG-CMV1 and TransFast (manufactured by Promega) in accordance with the protocol, a gene was introduced into COS-7 cell which had been cultured in a 100 mm culture dish to reach a 70% confluent stage. The supernatant after culturing for 3 days was recovered and filtered through a 0.22 μm filter, and then 100 μl of Anti-FLAG M2-Agarose Affinity Gel (manufactured by Sigma) was added to 10 ml of the supernatant and mixed on a roller at 4° C. overnight. After the reaction, the gel was washed three times with 50 mmol/l Tris-HCl, pH 7.4/20% glycerol, and then excess wash water was removed by using a syringe with a 27G injection needle. This gel was suspended in 50 mmol/l Tris-HCl, pH 7.4/20% glycerol/10 mmol/l phenylmethylsulfonyl fluoride/1 μg/ml leupeptin/1 μg/ml pepstatin to give a concentration of 50% (v/v), followed by centrifugation, and then the supernatant was discarded to obtain an enzyme-adsorbed gel suspension.

EXAMPLE 2

Elongation of Chondroitin Backbone Using the Enzyme of the Present Invention (1) Preparation of Chondroitin/Chondroitin Sulfate Odd-Numbered Saccharide Chondroitin (shark-derived chondroitin sulfate was chemically de-sulfated: manufactured by Seikagaku Corporation) and chondroitin sulfate (cartilage derived from shark: manufactured by Seikagaku Corporation) were limitedly digested with bovine testicle hyaluronidase (manufactured by Sigma), and then the reaction solution was kept at 100° C. for 10 minutes to heat-inactivate the enzyme. This reaction solution was applied to Superdex 30 column (60×1.6 cm: manufactured by Amersham Bioscience, chromatography conditions; mobile phase: 0.2 mol/l $NH_4HCO_3$, flow rate: 2 ml/minute), and the eluates were fractionated at 2 ml while monitoring at an absorbance of 225 nm to pool fractions corresponding to deca-saccharides. Each fraction was desalted by using PD10 column (manufactured by Amersham Bioscience), and uronic acid was determined by the carbazole-sulfuric acid method in accordance with the usual method, followed by freeze-drying. The freeze-dried samples were dissolved in distilled water to give a concentration of 1 mmol/l and used as even-numbered oligosaccharide samples (the chondroitin-derived deca-saccharide is referred to as "CH10", and the chondroitin sulfate-derived deca-saccharide is referred to as "CS10").

To 50 mmol/l MES buffer (pH 6.5) containing 10 nmol/l $MnCl_2$ and 171 μmol of ATP sodium salt, 10 μl of the enzyme-adsorbed gel suspension, 1 nmol of a substance to be tested (chondroitin (CHEL), chondroitin sulfate (CSEL), CH10 or CS10) and 0.036 nmol of [$^3$H]UDP-GalNAc were added, and the total volume was adjusted to 30 μl. The enzyme reaction was carried out at 37° C. for 1 hour, and then the reaction was stopped by keeping the reaction solution at 100° C. for 1 minute to inactivate the enzyme.

Each reaction solution was filtered through a microfilter of 0.22 μm in pore size (manufactured by Millipore) and then separated by Superdex peptide column (30×1.0 cm: manufactured by Amersham Bioscience, chromatography conditions; mobile phase: 0.2 mol/l NaCl, flow rate: 1.0 ml/minute), and the eluates were fractionated at 0.5 ml to measure the radioactivity by using a scintillation counter (FIG. 1). As a result, strong GalNAc transferring activity was observed when CHEL (17th to 18th fractions), CH10 (23rd fraction) and CS10 (23rd fraction) were used as the GalNAc acceptor substrates, while GalNAc transferring activity was not observed for CSEL (16th fraction). The 23rd fraction of the reaction products obtained from CH10 and CS10 were fractions showing molecular weights of eluted undeca-saccharides. The undeca-saccharide obtained from CH10 is referred to as "CH11", and the undeca-saccharide obtained from CS10 is referred to as "CS11".

The 21st to 25th fractions of CS11 were pooled and desalted by using PD10 column. The thus obtained sample was divided into two equal parts and freeze-dried. One of the bisected parts was dissolved in 100 µl of 0.1 mol/l Tris-HCl buffer (pH 7.4) containing 30 mmol/l sodium acetate (CS11A), and another was digested with chondroitinase ACII (100 mU of chondroitinase ACII (manufactured by Seikagaku Corporation) was dissolved in 100 µl of CS11 fraction, followed by enzymatic digestion at 37° C. for 10 hours and then heating to inactivate the enzyme: CS11B).

Figure 2:
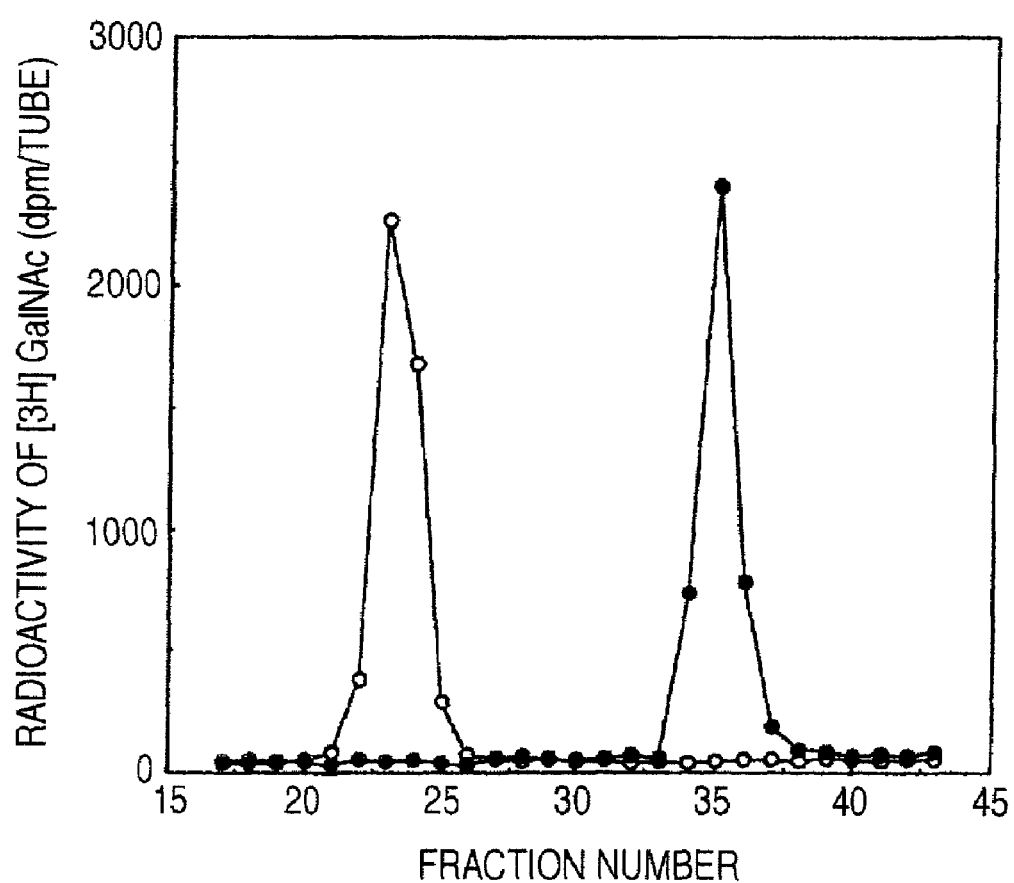
FIG. 2 is a graph showing a chromatography chart of a undeca-saccharide prepared by the GalNAc transferring activity of the enzyme of the present invention and its chondroitinase ACII digests. Open circles represent a chart of chondroitinase ACII-undigested undeca-saccharide, and closed circles represent a chart of digested product after chondroitinase ACII digestion.

CS11A and CS11B were filtered through a microfilter of 0.22 µm in pore size (manufactured by Millipore) and then separated by Superdex peptide column (30×10 mm: manufactured by Amersham Bioscience, chromatography conditions; mobile phase: 0.2 mol/l NaCl, flow rate: 0.5 ml/minute) and the eluates were fractionated at 0.5 ml, and when the radioactivity was measured by using a scintillation counter, the radioactivity peak was shifted to the trisaccharide fraction in CS11B (FIG. 2). It was found from this result that the enzyme of the present invention can prepare a undeca-saccharide by transferring GalNAc through a β1,4 bond to GlcUA of the non-reducing end of the chondroitin sulfate-derived deca-saccharide.

(2) Preparation of Chondroitin/Chondroitin Sulfate Even-Numbered Saccharides

Chondroitin (shark-derived chondroitin sulfate was chemically de-sulfated: manufactured by Seikagaku Corporation) and chondroitin sulfate (derived from shark cartilage: manufactured by Seikagaku Corporation) were limitedly digested with bovine testicle hyaluronidase (manufactured by Sigma), and then the reaction solution was kept at 100° C. for 10 minutes to heat-inactivate the enzyme. This reaction solution was centrifuged at 10,000×g for 10 minutes, and the supernatant was recovered and further digested with a bovine liver-derived β-glucuronidase (manufactured by Sigma). The enzyme reaction was stopped by keeping the reaction solution at 100° C. for 10 minutes. This reaction solution was applied to Superdex 30 column (60×1.6 cm: manufactured by Amersham Bioscience, chromatography conditions; mobile phase: 0.2 mol/l $NH_4HCO_3$, flow rate: 2 ml/minute), and the eluates were fractionated at 2 ml while monitoring at an absorbance of 225 nm to pool fractions corresponding to undeca-saccharides. Each fraction was desalted by using PD10 column (manufactured by Amersham Bioscience), and uronic acid was determined by the carbazole-sulfuric acid method in accordance with the usual method, followed by freeze-drying. The freeze-dried samples were dissolved in distilled water to give a concentration of 1 mmol/l and used as odd-numbered oligosaccharide samples (the chondroitin-derived undeca-saccharide: "CH11", the chondroitin sulfate-derived undeca-saccharide: "CS11").

Also, chondroitin (shark chondroitin sulfate was chemically de-sulfated: manufactured by Seikagaku Corporation) and chondroitin sulfate (derived from shark cartilage: manufactured by Seikagaku Corporation) were digested with bovine liver-derived β-glucuronidase (manufactured by Sigma) to prepare samples (referred to as "CHOL" and "CSOL", respectively).

To 50 mmol/l acetate buffer (pH 5.6) containing 10 nmol/l of $MnCl_2$, 10 µl of the enzyme-adsorbed gel suspension, 1 nmol of a substance to be tested (CHOL, CSOL, CH11 or CS11) and 0.432 nmol of [$^{14}$C]UDP-GlcUA were added, and the total volume was adjusted to 30 µl. The enzyme reaction was carried out at 37° C. for 1 hour, and then the reaction was stopped by keeping the reaction solution at 100° C. for 1 minute to inactivate the enzyme.

Figure 3:
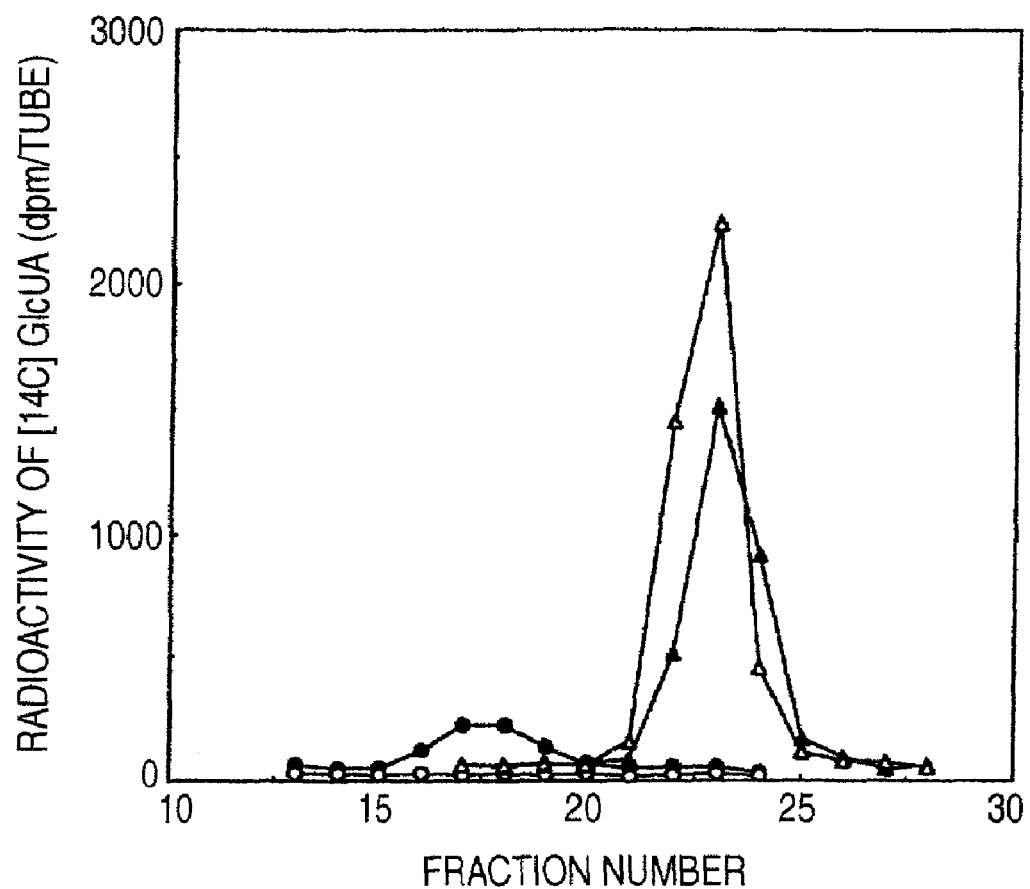
FIG. 3 is a graph showing a chromatography chart showing synthesis of even-numbered saccharides by the GlcUA transfer activity of the enzyme of the present invention. Open circles represent a chart showing the GlcUA transfer activity upon chondroitin sulfate, closed circles represent a chart showing the GlcUA transfer activity upon chondroitin, open triangles represent a chart showing the GlcUA transfer activity upon chondroitin sulfate undeca-saccharide, and closed triangles represent a chart showing the GlcUA transfer activity upon chondroitin undeca-saccharide.

Each reaction solution was filtered through a microfilter of 0.22 µm in pore size (manufactured by Millipore) and then separated by Superdex peptide column (30×1.0 cm: manufactured by Amersham Bioscience, chromatography conditions; mobile phase: 0.2 mol/l NaCl, flow rate: 0.5 ml/minute), and the eluates were fractionated at 0.5 ml to measure the radioactivity by using a scintillation counter (FIG. 3). As a result, strong GlcUA transferring activity was observed when CHOL (17th to 18th fractions), CH11 (23rd fraction) and CS11 (23rd fraction) were used as the GlcUA acceptor substrates, while the GlcUA transferring activity was not observed for CSOL (16th fraction). The 22nd and 23rd fractions of the reaction products obtained from CH11 and CS11 were fractions showing molecular weights of eluted dodeca-saccharides. The dodeca-saccharide obtained from CH11 is referred to as "CH12", and the dodeca-saccharide obtained from CS11 is referred to as "CS12".

The 21st to 25th fractions of CS12 were pooled and desalted by using PD10 column. The thus obtained sample was divide into two equal parts and freeze-dried. One of the bisected parts was dissolved in 100 µl of 0.1 mol/l Tris-HCl buffer (pH 7.4) containing 30 mmol/l sodium acetate (CS12A), and another was digested with chondroitinase ACII (100 mU of chondroitinase ACII (manufactured by Seikagaku Corporation) was dissolved in 100 µl of CS11 fraction, followed by enzymatic digestion at 37° C. for 10 hours and then heating to inactivate the enzyme: CS12B).

Figure 4:
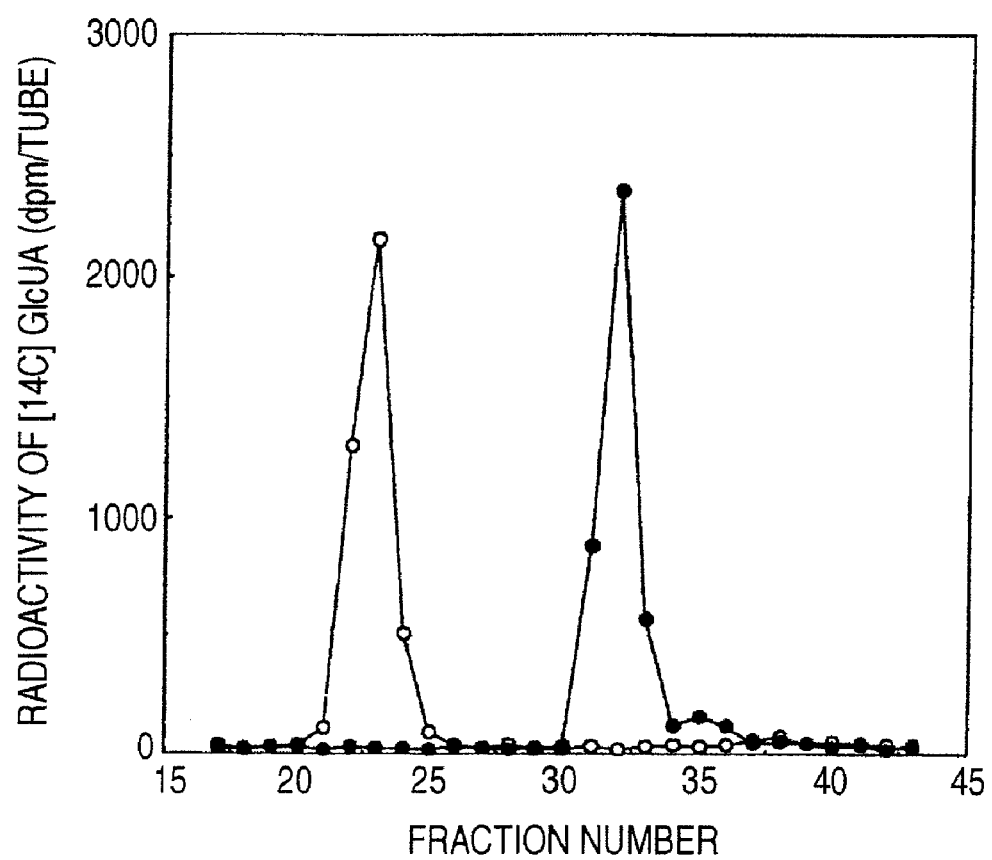
FIG. 4 is a graph showing a chromatography chart of a dodeca-saccharide prepared by the GlcUA transferring activity of the enzyme of the present invention and its chondroitinase ACII digests. Open circles represent a chart of chondroitinase ACII-undigested dodeca-saccharide, and closed circles represent a chart of digested product after chondroitinase ACII digestion.

CS12A and CS12B were filtered through a microfilter of 0.22 µm in pore size (manufactured by Millipore) and then separated by Superdex peptide column (30×1.0 cm: manufactured by Amersham Bioscience, chromatography conditions; mobile phase: 0.2 mol/l NaCl, flow rate: 0.5 ml/minute) and the eluates were fractionated at 0.5 ml, and when the radioactivity was measured by using a scintillation counter, the radioactivity peak was shifted to the disaccharide fraction in CS12B (FIG. 4). It was found from this result that the enzyme of the present invention can prepare a dodeca-saccharide by transferring GlcUA through a β1,3 bond to the chondroitin sulfate-derived undeca-saccharide.

A chondroitin sulfate-derived octa-saccharide and nona-saccharide were prepared in the same manner as described above, and as a result that they were used as the GlcUA acceptor and the GalNAc acceptor, it was found that they have activity of transferring a sugar residue in the same manner.

EXAMPLE 3

The GlcUA and GalNAc transferring activities of the enzyme of the present invention of Example 2 were checked for their optimum pH by changing the pH of buffers. An acetate buffer, an MES buffer, an imidazole buffer and a Tris-HCl buffer were used at a final concentration of 50 mmol/l for each buffer.

Figure 5:
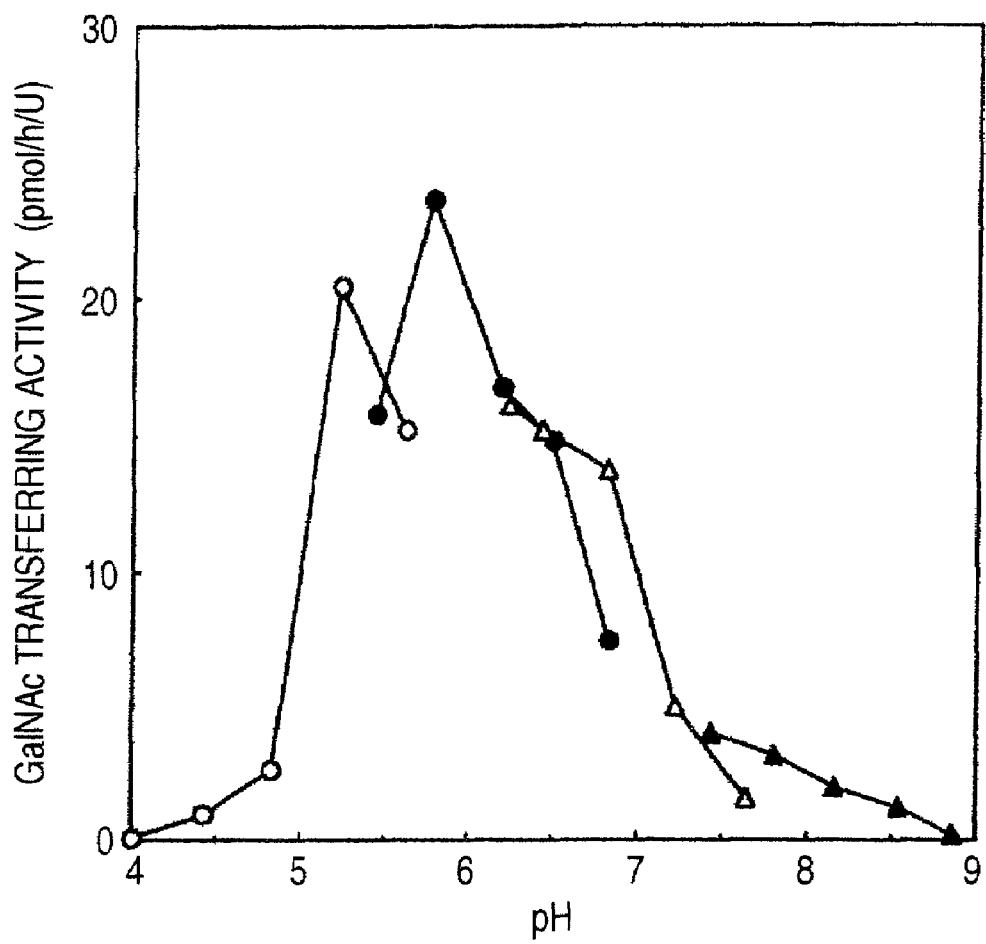
FIG. 5 is a graph showing optimum pH of the GlcUA transferring activity of the enzyme of the present invention. Open circles represent the optimum pH using an acetate buffer, closed circles represent the optimum pH using an MES buffer, open triangles represent the optimum pH using an imidazole buffer, and closed triangles represent the optimum pH using a Tris buffer.
Figure 6:
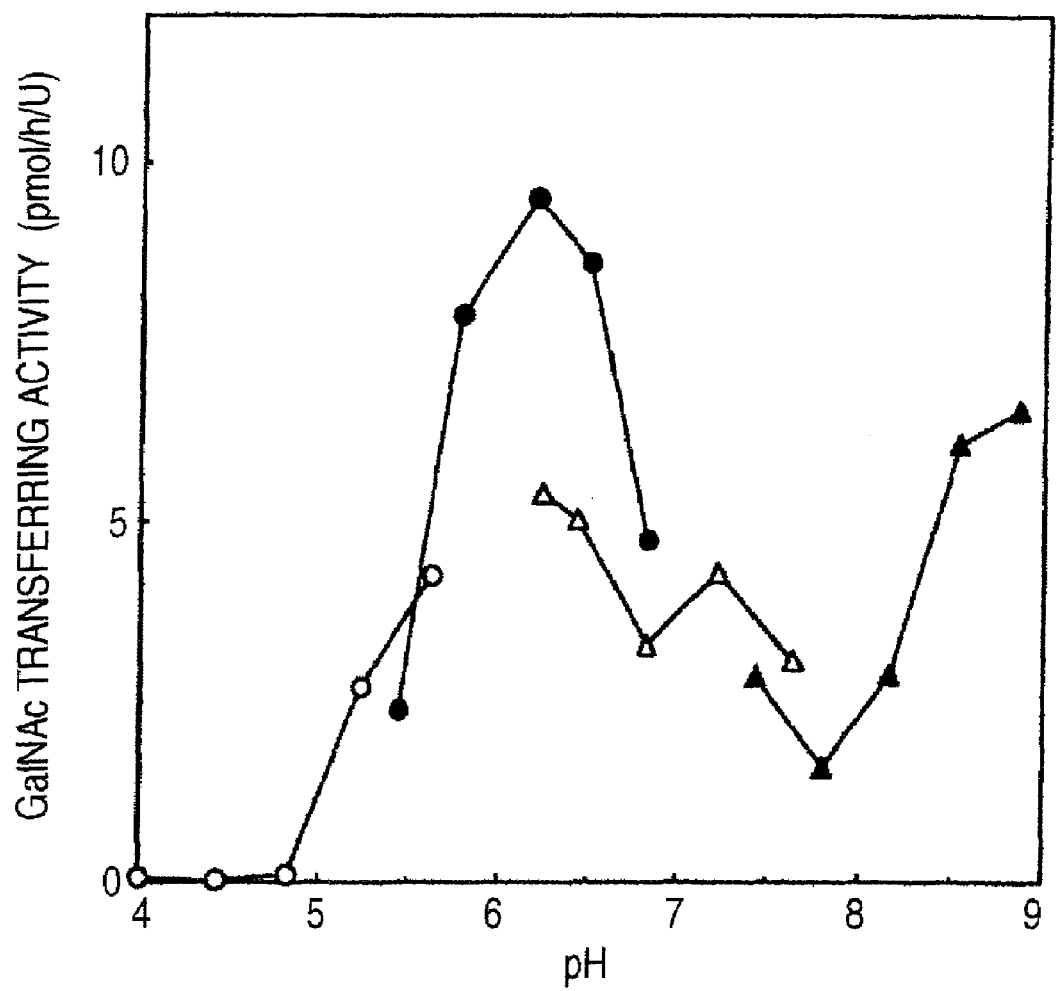
FIG. 6 is a graph showing optimum pH of the GalNAc transferring activity of the enzyme of the present invention. Open circles represent the optimum pH using an acetate buffer, closed circles represent the optimum pH using an MES buffer, open triangles represent the optimum pH using an imidazole buffer, and closed triangles represent the optimum pH using a Tris buffer.

As a result, it was found that the optimum pH of the GlcUA transferring activity was 5.8 (FIG. 5), and the optimum pH of the GalNAc transferring activity was 6.2 (FIG. 6).

EXAMPLE 4

Figure 7:
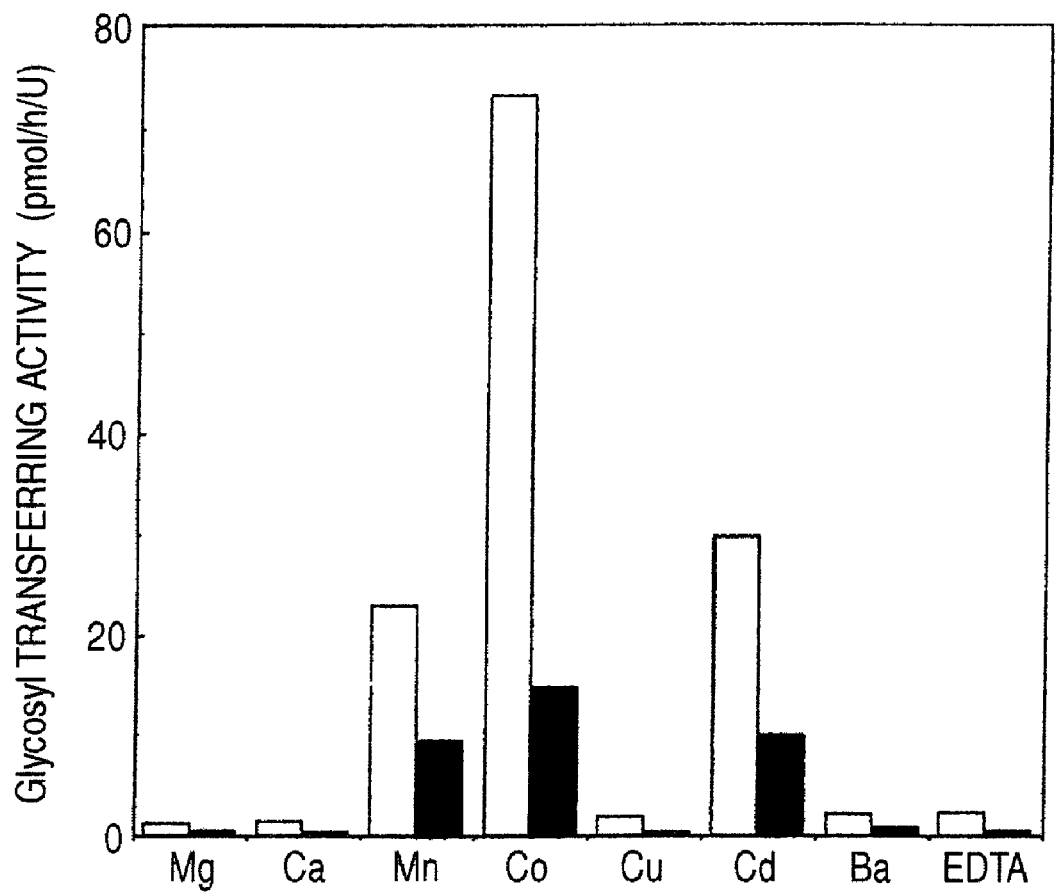
FIG. 7 is a graph showing influence of divalent cations upon the activities of the enzyme of the present invention. Open bars represent the GlcUA transferring activity, and closed bars represent the GalNAc transferring activity.

Under the measuring conditions for the GlcUA transferring activity and GalNAc transferring activity of the enzyme of the present invention of Example 2, the GlcUA transferring activity and GalNAc transferring activity were examined by adding 10 mmol/l ethylenediaminetetraacetic acid (EDTA) to the reaction system to find that the enzyme activities were completely lost (FIG. 7). Thus, it was found that the enzyme of the present invention requires a divalent cation for its activities.

Also, it was found that high enzyme activities were obtained when 10 mmol/l $CoCl_2$ or $CdCl_2$ was added to the reaction system instead of $MnCl_2$ (FIG. 7).

Figure 8:
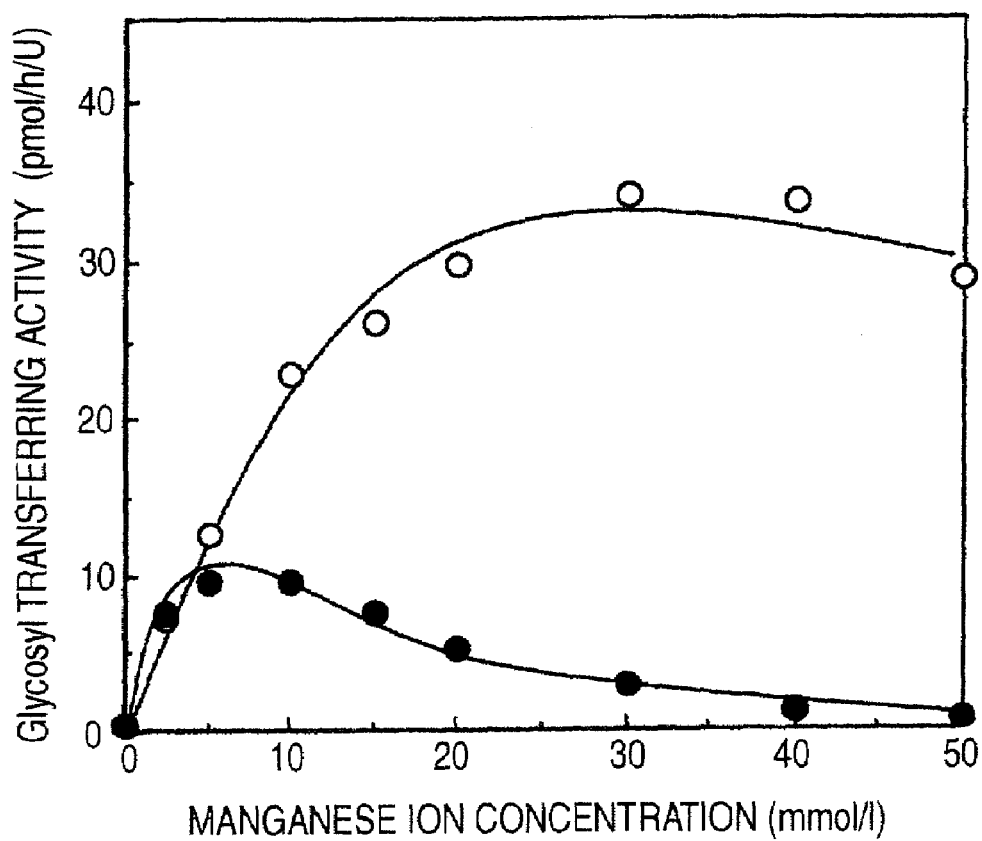
FIG. 8 is a graph showing influence of a manganese ion concentration upon the activities of the enzyme of the present invention. Open circles represent influence upon the GlcUA transferring activity of the enzyme of the present invention, and closed circles represent influence upon the GalNAc transferring activity of the enzyme of the present invention.

In addition, in order to examine influence of the concentration of a manganese ion upon activities of the enzyme of the present invention, the GlcUA transferring activity and GalNAc transferring activity were measured in the same manner by changing the final concentration of a manganese ion within the range of from 0 to 50 mmol/l under the reaction conditions of Example 2, which found that the optimum manganese ion concentrations for the GlcUA transferring activity and GalNAc transferring activity were 20 to 30 mmol/l and 5 to 10 mmol/l, respectively (FIG. 8).

EXAMPLE 5

Figure 9:
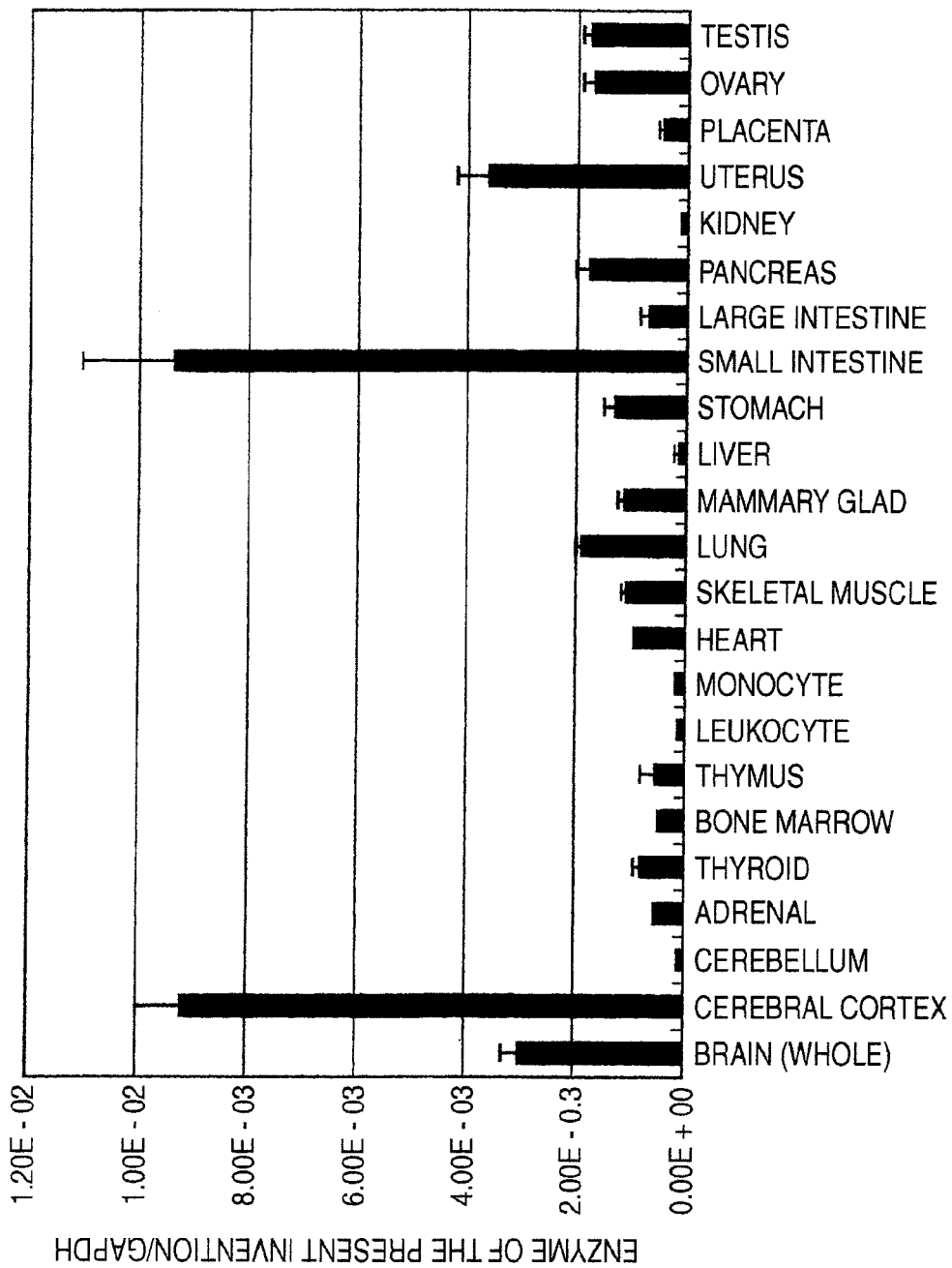
FIG. 9 is a graph showing determined values of the expression of the enzyme of the present invention in respective tissues of healthy person.

Analysis of Expression Pattern of the Gene of the Present Invention in Human Tissues In order to analyze the expressed level of the gene of the present invention in various human tissues, a real time PCR method (RT-PCR) was used. Amplification and determination were carried out by using various types of Marathon-Ready cDNA (manufactured by Clontech) as the template, two primers (SEQ ID NO:9 and SEQ ID NO:10) and a probe (SEQ ID NO:11) in which a miner groove binder (manufactured by Applied Biosystems) was bound to the 3' end. As the standard gene, a plasmid pCR2.1 (manufactured by Invitrogen) containing glyceraldehyde triphosphate dehydrogenase (GAPDH) was used by making a dilution series and thereby preparing a calibration curve. In addition, ABI PRISM 7700 (manufactured by Applied Biosystems) was used in the RT-PCR (FIG. 9).

As a result, it was found that the gene of the present invention is potently expressed in the whole brain, and uterus, particularly in the cerebral cortex and small intestines.

While the present invention has been described in detail and with reference to specific embodiments thereof, it will be apparent to one of skill in the art that various changes and modifications can be made therein without departing from the spirit and scope thereof. All references cited herein are incorporated in their entirety.

This application is based on Japanese application Nos. 2002-160855 and 2003-128344 filed on May 31, 2003 and May 6, 2003, respectively, the entire contents of which are incorporated hereinto by reference.

INDUSTRIAL APPLICABILITY

The present invention provides a human-derived novel chondroitin synthase, which is an enzyme for synthesizing a fundamental backbone of chondroitin and has both glucuronic acid transferase activity and N-acetylgalactosamine transferase activity.

FREE TEXT OF SEQUENCE LISTING

SEQ ID NO:3—Explanation of synthetic sequence: Synthetic DNA

SEQ ID NO:4—Explanation of synthetic sequence: Synthetic DNA

SEQ ID NO:5—Explanation of synthetic sequence: Synthetic DNA

SEQ ID NO:6—Explanation of synthetic sequence: Synthetic DNA

SEQ ID NO:7—Explanation of synthetic sequence: Synthetic DNA

SEQ ID NO:8—Explanation of synthetic sequence: Synthetic DNA

SEQ ID NO:9—Explanation of synthetic sequence: Synthetic DNA

SEQ ID NO:10—Explanation of synthetic sequence: Synthetic DNA

SEQ ID NO:11—Explanation of synthetic sequence: Synthetic DNA

---

The invention claimed is:

1. An isolated nucleic acid encoding chondroitin synthase, wherein the chondroitin synthase consists of a polypeptide consisting of the amino acid sequence of SEQ ID NO:2 or an amino acid sequence consisting of amino acid numbers 130 to 882 in the amino acid sequence of SEQ ID NO:2, or a sugar chain-bound polypeptide in which a sugar chain is bound to the polypeptide consisting of the amino acid sequence of SEQ ID NO:2 or is bound to the amino acid sequence consisting of amino acid numbers 130 to 882 in the amino acid sequence of SEQ ID NO:2.

2. An expression vector which comprises the nucleic acid according to claims 1.

3. The expression vector according to claim 2, which is capable of being expressed in a eucaryotic cell.

4. An isolated transformed cell which comprises the expression vector according to claim 2.

5. An isolated transformed cell which comprises the expression vector according to claim 3.

6. A process for producing a chondroitin synthase, which comprises growing the transformed cell according to claim 4 to produce and accumulate a chondroitin synthase and recovering the chondroitin synthase.

7. A process for producing a chondroitin synthase, which comprises growing the transformed cell according to claim 5 to produce and accumulate a chondroitin synthase and recovering the chondroitin synthase.

* * * * *

SEQUENCE LISTING

```
<160> NUMBER OF SEQ ID NOS: 11

<210> SEQ ID NO 1
<211> LENGTH: 2649
<212> TYPE: DNA
<213> ORGANISM: Homo sapiens
<220> FEATURE:
<221> NAME/KEY: CDS
<222> LOCATION: (1)..(2649)

<400> SEQUENCE: 1 atg gct gtg cgc tct cgc cgc ccg tgg atg agc gtg gca tta ggg ctg      48
Met Ala Val Arg Ser Arg Arg Pro Trp Met Ser Val Ala Leu Gly Leu
 1               5                  10                  15 gtg ctg ggc ttc acc gcc gcg tcc tgg ctc atc gcc ccc agg gtg gcg      96
Val Leu Gly Phe Thr Ala Ala Ser Trp Leu Ile Ala Pro Arg Val Ala
```

```
                20                  25                  30
gag ctg agc gag agg aag aga cgt ggc tcc agc ctc tgc tcc tac tac      144
Glu Leu Ser Glu Arg Lys Arg Arg Gly Ser Ser Leu Cys Ser Tyr Tyr
         35                  40                  45 ggt cgc tct gct gct ggc ccc cgc gcc ggc gct cag cag ccg ctc ccc      192
Gly Arg Ser Ala Ala Gly Pro Arg Ala Gly Ala Gln Gln Pro Leu Pro
 50                  55                  60 cag ccc cag tcc cga cca cgg cag gag cag tcg ccg ccc ccc gcg cgc      240
Gln Pro Gln Ser Arg Pro Arg Gln Glu Gln Ser Pro Pro Pro Ala Arg
 65                  70                  75                  80 cag gat ctc cag ggg cca ccg ctg ccc gag gca gca ccc ggg atc acc      288
Gln Asp Leu Gln Gly Pro Pro Leu Pro Glu Ala Ala Pro Gly Ile Thr
                 85                  90                  95 agt ttt cga agc agc ccc tgg cag cag cca cct ccg ctg cag cag cgg      336
Ser Phe Arg Ser Ser Pro Trp Gln Gln Pro Pro Pro Leu Gln Gln Arg
             100                 105                 110 cgg cga gga cgc gag cct gag ggc gcg acg ggg ctt ccc ggt gct cca      384
Arg Arg Gly Arg Glu Pro Glu Gly Ala Thr Gly Leu Pro Gly Ala Pro
         115                 120                 125 gcg gcc gag ggg gag ccc gag gag gag gac ggg ggc gcg gct ggg cag      432
Ala Ala Glu Gly Glu Pro Glu Glu Glu Asp Gly Gly Ala Ala Gly Gln
130                 135                 140 cgg aga gac ggc cgg ccg ggg agt agc cac aac ggc agc ggg gac ggg      480
Arg Arg Asp Gly Arg Pro Gly Ser Ser His Asn Gly Ser Gly Asp Gly
145                 150                 155                 160 ggc gct gcc gcc ccg agc gcc cga ccc cgg gac ttc ctg tac gtg ggg      528
Gly Ala Ala Ala Pro Ser Ala Arg Pro Arg Asp Phe Leu Tyr Val Gly
                 165                 170                 175 gtg atg acc gcg cag aag tac ctg ggc agc cgc gcg ctg gcc gcg cag      576
Val Met Thr Ala Gln Lys Tyr Leu Gly Ser Arg Ala Leu Ala Ala Gln
             180                 185                 190 cgg acc tgg gcg cgt ttc atc ccg ggc cgc gtg gag ttc ttt tcc agc      624
Arg Thr Trp Ala Arg Phe Ile Pro Gly Arg Val Glu Phe Phe Ser Ser
         195                 200                 205 cag cag ccc ccc aac gcc ggc cag ccc ccg cca ccc ctg cct gtc atc      672
Gln Gln Pro Pro Asn Ala Gly Gln Pro Pro Pro Pro Leu Pro Val Ile
210                 215                 220 gcg cta ccg ggt gtg gac gac tcc tat cct ccc cag aaa aag tcc ttc      720
Ala Leu Pro Gly Val Asp Asp Ser Tyr Pro Pro Gln Lys Lys Ser Phe
225                 230                 235                 240 atg atg atc aag tac atg cac gac cac tac ctg gac aag tat gag tgg      768
Met Met Ile Lys Tyr Met His Asp His Tyr Leu Asp Lys Tyr Glu Trp
                 245                 250                 255 ttc atg cgc gcc gac gac gat gtc tac atc aaa ggt gat aaa tta gaa      816
Phe Met Arg Ala Asp Asp Asp Val Tyr Ile Lys Gly Asp Lys Leu Glu
             260                 265                 270 gag ttt ctt aga tcg cta aac agc agt aag cct ctc tac ctg gga cag      864
Glu Phe Leu Arg Ser Leu Asn Ser Ser Lys Pro Leu Tyr Leu Gly Gln
         275                 280                 285 act ggc ctg ggg aat att gaa gag ctt gga aag ctg gga ctg gag cct      912
Thr Gly Leu Gly Asn Ile Glu Glu Leu Gly Lys Leu Gly Leu Glu Pro
290                 295                 300 ggg gaa aac ttc tgt atg gga gga cct ggc atg atc ttt agc cga gaa      960
Gly Glu Asn Phe Cys Met Gly Gly Pro Gly Met Ile Phe Ser Arg Glu
305                 310                 315                 320 gtt ctc agg agg atg gtg cca cat att ggt gaa tgc ttt aga gaa atg     1008
Val Leu Arg Arg Met Val Pro His Ile Gly Glu Cys Leu Arg Glu Met
                 325                 330                 335 tac acg act cat gag gat gtg gaa gta gga aga tgc gtt cgc cgt ttt     1056
```

```
                                                              -continued

Tyr Thr Thr His Glu Asp Val Glu Val Gly Arg Cys Val Arg Arg Phe
        340                 345                 350 ggt ggg act cag tgt gtc tgg tct tac gag atg caa caa ctg ttc cat    1104
Gly Gly Thr Gln Cys Val Trp Ser Tyr Glu Met Gln Gln Leu Phe His
            355                 360                 365 gaa aat tat gaa cac aat cgg aag ggt tac atc caa gac ctt cac aat    1152
Glu Asn Tyr Glu His Asn Arg Lys Gly Tyr Ile Gln Asp Leu His Asn
        370                 375                 380 agc aaa atc cat gca gcc ata aca ctt cat ccc aac aaa agg cct gca    1200
Ser Lys Ile His Ala Ala Ile Thr Leu His Pro Asn Lys Arg Pro Ala
385                 390                 395                 400 tac caa tac agg ctg cat aat tac atg ctc agc cgc aaa att tct gaa    1248
Tyr Gln Tyr Arg Leu His Asn Tyr Met Leu Ser Arg Lys Ile Ser Glu
                405                 410                 415 ctt cgc tac cgc acc atc cag ctc cac agg gaa agt gcc ctg atg agc    1296
Leu Arg Tyr Arg Thr Ile Gln Leu His Arg Glu Ser Ala Leu Met Ser
            420                 425                 430 aag ctc agt aac aca gaa gtg agc aaa gag gac cag cag ctg gga gtg    1344
Lys Leu Ser Asn Thr Glu Val Ser Lys Glu Asp Gln Gln Leu Gly Val
        435                 440                 445 ata cct tct ttc aac cac ttc cag cct cgg gag aga aat gaa gtg ata    1392
Ile Pro Ser Phe Asn His Phe Gln Pro Arg Glu Arg Asn Glu Val Ile
    450                 455                 460 gaa tgg gag ttc ctg aca ggg aag ctt cta tac tca gca gct gag aac    1440
Glu Trp Glu Phe Leu Thr Gly Lys Leu Leu Tyr Ser Ala Ala Glu Asn
465                 470                 475                 480 cag ccc cct cga cag agc ctc agt agc att tta aga aca gca ctg gat    1488
Gln Pro Pro Arg Gln Ser Leu Ser Ser Ile Leu Arg Thr Ala Leu Asp
                485                 490                 495 gat acc gtc cta cag gtg atg gag atg atc aat gag aat gcc aag agc    1536
Asp Thr Val Leu Gln Val Met Glu Met Ile Asn Glu Asn Ala Lys Ser
            500                 505                 510 aga gga cgg ctc att gac ttc aag gaa att cag tat ggc tac cgc aga    1584
Arg Gly Arg Leu Ile Asp Phe Lys Glu Ile Gln Tyr Gly Tyr Arg Arg
        515                 520                 525 gtt aac ccc atg cac ggg gtg gag tac att ttg gat tta ctc ctt tta    1632
Val Asn Pro Met His Gly Val Glu Tyr Ile Leu Asp Leu Leu Leu Leu
    530                 535                 540 tac aaa aga cac aag gga agg aaa ctg act gtg cca gtg aga cgt cat    1680
Tyr Lys Arg His Lys Gly Arg Lys Leu Thr Val Pro Val Arg Arg His
545                 550                 555                 560 gcc tat ctt cag cag ttg ttc agc aag cct ttc ttc aga gag acc gaa    1728
Ala Tyr Leu Gln Gln Leu Phe Ser Lys Pro Phe Phe Arg Glu Thr Glu
                565                 570                 575 gag cta gat gtc aac agt ctt gtg gag agt att aac agt gaa act cag    1776
Glu Leu Asp Val Asn Ser Leu Val Glu Ser Ile Asn Ser Glu Thr Gln
            580                 585                 590 tca ttc tcc ttt ata tct aat tct tta aag ata tta tct tct ttt caa    1824
Ser Phe Ser Phe Ile Ser Asn Ser Leu Lys Ile Leu Ser Ser Phe Gln
        595                 600                 605 ggt gcc aaa gaa atg gga ggg cac aat gaa aag aaa gta cac att ctc    1872
Gly Ala Lys Glu Met Gly Gly His Asn Glu Lys Lys Val His Ile Leu
    610                 615                 620 gtt cct ctc atc gga agg tat gac att ttc ttg aga ttc atg gag aac    1920
Val Pro Leu Ile Gly Arg Tyr Asp Ile Phe Leu Arg Phe Met Glu Asn
625                 630                 635                 640 ttt gaa aac atg tgt ctt atc cca aag cag aat gta aag ttg gtc att    1968
Phe Glu Asn Met Cys Leu Ile Pro Lys Gln Asn Val Lys Leu Val Ile
                645                 650                 655
```

```
atc ctt ttc agt agg gat tct ggc caa gac tcc agc aag cat att gag   2016
Ile Leu Phe Ser Arg Asp Ser Gly Gln Asp Ser Ser Lys His Ile Glu
            660                 665                 670 ctg ata aaa ggg tac cag aac aag tac ccc aaa gca gaa atg acc ctg   2064
Leu Ile Lys Gly Tyr Gln Asn Lys Tyr Pro Lys Ala Glu Met Thr Leu
        675                 680                 685 atc cca atg aag gga gag ttt tcc aga ggt ctt ggt ctt gaa atg gct   2112
Ile Pro Met Lys Gly Glu Phe Ser Arg Gly Leu Gly Leu Glu Met Ala
    690                 695                 700 tct gcc cag ttt gac aat gac act ttg ctg cta ttt tgt gat gtt gac   2160
Ser Ala Gln Phe Asp Asn Asp Thr Leu Leu Leu Phe Cys Asp Val Asp
705                 710                 715                 720 ttg atc ttc aga gaa gat ttt ctc caa cga tgt aga gac aat aca att   2208
Leu Ile Phe Arg Glu Asp Phe Leu Gln Arg Cys Arg Asp Asn Thr Ile
                725                 730                 735 cag gga caa cag gtg tac tat ccc atc atc ttt agc cag tat gac cca   2256
Gln Gly Gln Gln Val Tyr Tyr Pro Ile Ile Phe Ser Gln Tyr Asp Pro
            740                 745                 750 aag gta aca aac ggg gga aat cct ccc act gat ggt tac ttc ata ttc   2304
Lys Val Thr Asn Gly Gly Asn Pro Pro Thr Asp Gly Tyr Phe Ile Phe
        755                 760                 765 tca aaa aag act gga ttt tgg aga gac tat gga tat ggc atc acc tgt   2352
Ser Lys Lys Thr Gly Phe Trp Arg Asp Tyr Gly Tyr Gly Ile Thr Cys
    770                 775                 780 att tac aaa agt gat ctt cta ggt gca ggt gga ttt gat acc tca ata   2400
Ile Tyr Lys Ser Asp Leu Leu Gly Ala Gly Gly Phe Asp Thr Ser Ile
785                 790                 795                 800 caa ggc tgg gga cta gaa gat gta gat ctc tac aat aaa gtc att cta   2448
Gln Gly Trp Gly Leu Glu Asp Val Asp Leu Tyr Asn Lys Val Ile Leu
                805                 810                 815 tct ggc tta agg cca ttc aga agc caa gaa gta gga gtg gtg cat att   2496
Ser Gly Leu Arg Pro Phe Arg Ser Gln Glu Val Gly Val Val His Ile
            820                 825                 830 ttc cat cca gtt cat tgt gat cct aac ttg gac cct aag cag tat aag   2544
Phe His Pro Val His Cys Asp Pro Asn Leu Asp Pro Lys Gln Tyr Lys
        835                 840                 845 atg tgc tta gga tcc aag gca agt act ttc gcc tca acc atg caa ctg   2592
Met Cys Leu Gly Ser Lys Ala Ser Thr Phe Ala Ser Thr Met Gln Leu
    850                 855                 860 gct gaa ctc tgg ctt gaa aaa cat tta ggt gtc agg tac aat cga act   2640
Ala Glu Leu Trp Leu Glu Lys His Leu Gly Val Arg Tyr Asn Arg Thr
865                 870                 875                 880 ctc tcc tga                                                       2649
Leu Ser

<210> SEQ ID NO 2
<211> LENGTH: 882
<212> TYPE: PRT
<213> ORGANISM: Homo sapiens

<400> SEQUENCE: 2

Met Ala Val Arg Ser Arg Arg Pro Trp Met Ser Val Ala Leu Gly Leu
  1               5                  10                  15

Val Leu Gly Phe Thr Ala Ala Ser Trp Leu Ile Ala Pro Arg Val Ala
             20                  25                  30

Glu Leu Ser Glu Arg Lys Arg Gly Ser Ser Leu Cys Ser Tyr Tyr
         35                  40                  45

Gly Arg Ser Ala Ala Gly Pro Arg Ala Gly Ala Gln Gln Pro Leu Pro
     50                  55                  60
```

-continued

```
Gln Pro Gln Ser Arg Pro Arg Gln Glu Gln Ser Pro Pro Ala Arg
 65                  70                  75                  80

Gln Asp Leu Gln Gly Pro Pro Leu Pro Glu Ala Ala Pro Gly Ile Thr
             85                  90                  95

Ser Phe Arg Ser Ser Pro Trp Gln Gln Pro Pro Leu Gln Gln Arg
            100                 105                 110

Arg Arg Gly Arg Glu Pro Glu Gly Ala Thr Gly Leu Pro Gly Ala Pro
            115                 120                 125

Ala Ala Glu Gly Glu Pro Glu Glu Asp Gly Gly Ala Ala Gly Gln
130                 135                 140

Arg Arg Asp Gly Arg Pro Gly Ser Ser His Asn Gly Ser Gly Asp Gly
145                 150                 155                 160

Gly Ala Ala Ala Pro Ser Ala Arg Pro Arg Asp Phe Leu Tyr Val Gly
                165                 170                 175

Val Met Thr Ala Gln Lys Tyr Leu Gly Ser Arg Ala Leu Ala Ala Gln
            180                 185                 190

Arg Thr Trp Ala Arg Phe Ile Pro Gly Arg Val Glu Phe Phe Ser Ser
            195                 200                 205

Gln Gln Pro Pro Asn Ala Gly Gln Pro Pro Pro Leu Pro Val Ile
210                 215                 220

Ala Leu Pro Gly Val Asp Asp Ser Tyr Pro Pro Gln Lys Lys Ser Phe
225                 230                 235                 240

Met Met Ile Lys Tyr Met His Asp His Tyr Leu Asp Lys Tyr Glu Trp
                245                 250                 255

Phe Met Arg Ala Asp Asp Asp Val Tyr Ile Lys Gly Asp Lys Leu Glu
                260                 265                 270

Glu Phe Leu Arg Ser Leu Asn Ser Ser Lys Pro Leu Tyr Leu Gly Gln
            275                 280                 285

Thr Gly Leu Gly Asn Ile Glu Glu Leu Gly Lys Leu Gly Leu Glu Pro
            290                 295                 300

Gly Glu Asn Phe Cys Met Gly Gly Pro Gly Met Ile Phe Ser Arg Glu
305                 310                 315                 320

Val Leu Arg Arg Met Val Pro His Ile Gly Glu Cys Leu Arg Glu Met
                325                 330                 335

Tyr Thr Thr His Glu Asp Val Glu Val Gly Arg Cys Val Arg Arg Phe
                340                 345                 350

Gly Gly Thr Gln Cys Val Trp Ser Tyr Glu Met Gln Gln Leu Phe His
            355                 360                 365

Glu Asn Tyr Glu His Asn Arg Lys Gly Tyr Ile Gln Asp Leu His Asn
            370                 375                 380

Ser Lys Ile His Ala Ala Ile Thr Leu His Pro Asn Lys Arg Pro Ala
385                 390                 395                 400

Tyr Gln Tyr Arg Leu His Asn Tyr Met Leu Ser Arg Lys Ile Ser Glu
                405                 410                 415

Leu Arg Tyr Arg Thr Ile Gln Leu His Arg Glu Ser Ala Leu Met Ser
                420                 425                 430

Lys Leu Ser Asn Thr Glu Val Ser Lys Glu Asp Gln Gln Leu Gly Val
            435                 440                 445

Ile Pro Ser Phe Asn His Phe Gln Pro Arg Glu Arg Asn Glu Val Ile
            450                 455                 460

Glu Trp Glu Phe Leu Thr Gly Lys Leu Leu Tyr Ser Ala Ala Glu Asn
465                 470                 475                 480

Gln Pro Pro Arg Gln Ser Leu Ser Ser Ile Leu Arg Thr Ala Leu Asp
```

```
                    485                 490                 495
Asp Thr Val Leu Gln Val Met Glu Met Ile Asn Glu Asn Ala Lys Ser
            500                 505                 510

Arg Gly Arg Leu Ile Asp Phe Lys Glu Ile Gln Tyr Gly Tyr Arg Arg
            515                 520                 525

Val Asn Pro Met His Gly Val Glu Tyr Ile Leu Asp Leu Leu Leu Leu
            530                 535                 540

Tyr Lys Arg His Lys Gly Arg Lys Leu Thr Val Pro Val Arg Arg His
545                 550                 555                 560

Ala Tyr Leu Gln Gln Leu Phe Ser Lys Pro Phe Phe Arg Glu Thr Glu
                565                 570                 575

Glu Leu Asp Val Asn Ser Leu Val Glu Ser Ile Asn Ser Glu Thr Gln
            580                 585                 590

Ser Phe Ser Phe Ile Ser Asn Ser Leu Lys Ile Leu Ser Ser Phe Gln
                595                 600                 605

Gly Ala Lys Glu Met Gly Gly His Asn Glu Lys Lys Val His Ile Leu
            610                 615                 620

Val Pro Leu Ile Gly Arg Tyr Asp Ile Phe Leu Arg Phe Met Glu Asn
625                 630                 635                 640

Phe Glu Asn Met Cys Leu Ile Pro Lys Gln Asn Val Lys Leu Val Ile
                645                 650                 655

Ile Leu Phe Ser Arg Asp Ser Gly Gln Asp Ser Ser Lys His Ile Glu
                660                 665                 670

Leu Ile Lys Gly Tyr Gln Asn Lys Tyr Pro Lys Ala Glu Met Thr Leu
            675                 680                 685

Ile Pro Met Lys Gly Glu Phe Ser Arg Gly Leu Gly Leu Glu Met Ala
690                 695                 700

Ser Ala Gln Phe Asp Asn Asp Thr Leu Leu Leu Phe Cys Asp Val Asp
705                 710                 715                 720

Leu Ile Phe Arg Glu Asp Phe Leu Gln Arg Cys Arg Asp Asn Thr Ile
                725                 730                 735

Gln Gly Gln Gln Val Tyr Tyr Pro Ile Ile Phe Ser Gln Tyr Asp Pro
            740                 745                 750

Lys Val Thr Asn Gly Gly Asn Pro Pro Thr Asp Gly Tyr Phe Ile Phe
            755                 760                 765

Ser Lys Lys Thr Gly Phe Trp Arg Asp Tyr Gly Tyr Gly Ile Thr Cys
770                 775                 780

Ile Tyr Lys Ser Asp Leu Leu Gly Ala Gly Phe Asp Thr Ser Ile
785                 790                 795                 800

Gln Gly Trp Gly Leu Glu Asp Val Asp Leu Tyr Asn Lys Val Ile Leu
                805                 810                 815

Ser Gly Leu Arg Pro Phe Arg Ser Gln Glu Val Gly Val Val His Ile
            820                 825                 830

Phe His Pro Val His Cys Asp Pro Asn Leu Asp Pro Lys Gln Tyr Lys
                835                 840                 845

Met Cys Leu Gly Ser Lys Ala Ser Thr Phe Ala Ser Thr Met Gln Leu
            850                 855                 860

Ala Glu Leu Trp Leu Glu Lys His Leu Gly Val Arg Tyr Asn Arg Thr
865                 870                 875                 880

Leu Ser

<210> SEQ ID NO 3
<211> LENGTH: 26
```

```
<210> SEQ ID NO 3
<211> LENGTH: 26
<212> TYPE: DNA
<213> ORGANISM: Artificial Sequence
<220> FEATURE:
<223> OTHER INFORMATION: Chemically-synthesized 5' primer for PCR

<400> SEQUENCE: 3
cccaagcttg ccgaggggga gcccga                                            26

<210> SEQ ID NO 4
<211> LENGTH: 29
<212> TYPE: DNA
<213> ORGANISM: Artificial Sequence
<220> FEATURE:
<223> OTHER INFORMATION: Chemically-synthesized 3' primer for PCR

<400> SEQUENCE: 4
gctctagact gtcaggagag agttcgatt                                         29

<210> SEQ ID NO 5
<211> LENGTH: 25
<212> TYPE: DNA
<213> ORGANISM: Artificial Sequence
<220> FEATURE:
<223> OTHER INFORMATION: Chemically-synthesized 5' primer for PCR

<400> SEQUENCE: 5
atggctgtgc gctctcgccg cccgt                                             25

<210> SEQ ID NO 6
<211> LENGTH: 25
<212> TYPE: DNA
<213> ORGANISM: Artificial Sequence
<220> FEATURE:
<223> OTHER INFORMATION: Chemically-synthesized 3' primer for PCR

<400> SEQUENCE: 6
cgtccccgct gccgttgtgg ctact                                             25

<210> SEQ ID NO 7
<211> LENGTH: 25
<212> TYPE: DNA
<213> ORGANISM: Artificial Sequence
<220> FEATURE:
<223> OTHER INFORMATION: Chemically-synthesized 5' primer for PCR

<400> SEQUENCE: 7
agtagccaca acggcagcgg ggacg                                             25

<210> SEQ ID NO 8
<211> LENGTH: 24
<212> TYPE: DNA
<213> ORGANISM: Artificial Sequence
<220> FEATURE:
<223> OTHER INFORMATION: Chemically-synthesized 3' primer for PCR

<400> SEQUENCE: 8
tcaggagaga gttcgattgt acct                                              24

<210> SEQ ID NO 9
<211> LENGTH: 23
<212> TYPE: DNA
<213> ORGANISM: Artificial Sequence
<220> FEATURE:
<223> OTHER INFORMATION: Chemically-synthesized 5' primer for RT-PCR

<400> SEQUENCE: 9
```

-continued

```
cccagaaaaa gtccttcatg atg                                              23

<210> SEQ ID NO 10
<211> LENGTH: 30
<212> TYPE: DNA
<213> ORGANISM: Artificial Sequence
<220> FEATURE:
<223> OTHER INFORMATION: Chemically-synthesized 3' primer for RT-PCR

<400> SEQUENCE: 10
aactcttcta atttgtcacc tttgatgtag                                       30

<210> SEQ ID NO 11
<211> LENGTH: 17
<212> TYPE: DNA
<213> ORGANISM: Artificial Sequence
<220> FEATURE:
<223> OTHER INFORMATION: Chemically-synthesized probe for RT-PCR

<400> SEQUENCE: 11
atgagtggtt catgcgc                                                     17
```